United States Patent [19]

Ishii

[11] Patent Number: 5,273,898

[45] Date of Patent: Dec. 28, 1993

[54] THERMALLY STABLE AND POSITIONALLY NON-SPECIFIC LIPASE ISOLATED FROM CANDIDA

[75] Inventor: Michiyo Ishii, Sapporo, Japan

[73] Assignee: Noro Nordisk A/S, Bagsvaerd, Denmark

[21] Appl. No.: 962,621

[22] Filed: Oct. 16, 1992

Related U.S. Application Data

[63] Continuation of Ser. No. 206,344, Jul. 21, 1988, filed as PCT/DK87/00127, Oct. 16, 1987, abandoned.

[30] Foreign Application Priority Data

Oct. 17, 1986 [DK] Denmark .............................. 4966/86
Sep. 28, 1987 [DK] Denmark .............................. 5072/87

[51] Int. Cl.$^5$ .......................... C12P 7/64; C12N 9/20; C12N 1/00
[52] U.S. Cl. .................................... 435/198; 435/921; 435/134
[58] Field of Search ...................... 435/198, 921, 134

[56] References Cited

U.S. PATENT DOCUMENTS

| | | | |
|---|---|---|---|
| 3,619,372 | 11/1971 | Yoshida et al. | 435/198 |
| 3,898,130 | 8/1975 | Komatsu | 435/198 |
| 4,665,029 | 5/1987 | Iwai et al. | 435/198 |
| 4,826,767 | 5/1989 | Hansen | 435/198 |
| 4,943,530 | 7/1990 | Christner et al. | 435/198 |

FOREIGN PATENT DOCUMENTS

| | | | |
|---|---|---|---|
| 117553 | 9/1984 | European Pat. Off. | 435/198 |
| 0204284 | 12/1986 | European Pat. Off. | |
| 57-63087 | 4/1982 | Japan | 435/198 |
| 58-152481 | 9/1983 | Japan | 435/198 |
| 976415 | 11/1964 | United Kingdom . | |
| 1461408 | 1/1977 | United Kingdom . | |
| 1519126 | 6/1978 | United Kingdom . | |
| 2142337 | 1/1985 | United Kingdom . | |

*Primary Examiner*—David M. Naff
*Assistant Examiner*—Michael V. Meller
*Attorney, Agent, or Firm*—Steve T. Zelson; Elias J. Lambiris

[57] ABSTRACT

Thermally stable, positionally non-specific lipases native to Candida species of *C. antartica*, *C. tsukubaensis*, *C. auriculariae*, *C. humicola*, and *C. foliarum*, are isolated. The lipase of *C. antarctica*, is preferred. Two lipase activities are elaborated by *C. antarctica*. One lipase fraction being 43 kD in molecular weight, and of an isoelectric point of about 8.0 and has excellent thermostability. The other fraction being 33 kD in molecular weight and of an isoelectric point of about 6.0 and has high retention of residual activity at pH 10.

21 Claims, 6 Drawing Sheets

——— CAND. ANT. LIPASE
—·—·— LIPOZYME

THERMALLY STABLE AND POSITIONALLY NON-SPECIFIC LIPASE ISOLATED FROM CANDIDA

This application is a continuation application of co-pending application Ser. No. 07/206,344, filed Jul. 21, 1988, filed as PCT/DK87/00127, Oct. 16, 1987, now abandoned.

TECHNICAL FIELD

This invention is directed to novel positionally non-specific lipase of enhanced thermostability in soluble and immobilized form, to a method of producing it and to its use in ester hydrolysis, ester synthesis and interesterification.

DEFINITIONS

The following definitions of the underlined words shall apply in this specification with claims:

Lipase is taken to mean an enzyme that catalyzes reactions involving ester bonds (such as hydrolysis, synthesis and exchange of ester bonds) in water-insoluble carboxylic acid esters.

Immobilized lipase denotes lipase in the form of immobilized enzyme or immobilized cells, as defined in "Guidelines for the characterization of immobilized biocatalysts" (1983), Enzyme Microb. Technol., 5, 304–307. Derivatized lipase denotes lipase that has been chemically modified without immobilizing it. Soluble lipase denotes unmodified lipase that is neither immobilized nor derivatized.

A positionally specific lipase (or specific lipase for short) is one that reacts preferentially with the fatty acyl groups in the 1- and 3- positions of a triglyceride molecule, and a positionally non-specific lipase (or non-specific lipase for short) is one that reacts at comparable rates with all three fatty acyl groups of a triglyceride.

BACKGROUND ART

A wide variety of lipases of microbial origin (both intracellular and extracellular), as well as plant and animal origin are known. For a general discussion of extracellular microbial lipases, see A. R. Macrae, p. 225ff in Microbial Enzymes and Biotechnology (Ed. W. Fogarty), ISBN 0-85334-185-0, Applied Science Publishers Ltd., 1983.

Non-specific lipases from the following microorganisms are known: *Staphylococcus aureus* (Vadehra, D. V. (1974). Lipids, 9, 158), *Penicillium cyclopium* (Okumura, S., et al. (1976). Agricultural and Biological Chemistry, 40, 655 and Renshaw E. C. and San Clemente C. L. (1966) Developments in Industrial Microbiology, 8, 214), *Corynebacterium acnes* (Hassing, G. S. (1971). Biochimica et Biophysica Acta, 242, 381 and Pablo G. (1974) The Journal of Investigative Dermatology, 63, 231), *Propionibacterium acnes* (Ingham, E. et al. (1981). Journal of General Microbiology, 124, 393), *Candida cylindracea* (also known as *C. rugosa*) (Benzonana, G. & Esposito, S. (1971). Biochimica et Biophysica Acta, 231, 15; and Kimura Y. (1983) Eur. J. Appl. Microbiol. Biotechnol., 17, 107), *Candida curvata* (D. Montet et al. (1985), Fette Seifen Anstrichmittel, 87, 181). However, data in the literature referred to and in an example of this specification demonstrate that all these lipases have insufficient thermostability for long-term use at about 60° C. or higher. Also *S. aureus*, *C. acnes* and *P. acnes* are suspected or proven pathogens.

Lipase from *Geotrichum candidum* (Jensen, R. G. (1974) Lipids, 9, 149; Jensen, R. G. et al. (1972) Lipids, 7, 738; and Tsujisaka, Y. and Iwai, M. (1984) Kagaku to Kogyo, 58, 60) is positionally non-specific, but is highly specific for certain unsaturated fatty acyl groups. Further, it is not thermostable.

Further, lipases from *Humicola lanuginosa* (Liu, W. H., Beppu, T. & Arima, K. (1973). Agricultural and Biological Chemistry, 37, 1349) and *Chromobacterium viscosum* (Sugiura, M. & Isobe, M. (1975). Chemical and Pharmaceutical Bulletin, 23, 1226) have been described as non-specific. However, later results (Biotechnology and Genetic Engineering Reviews, Vol. 3 (Sep. 1985), page 200) show that these two lipases are, in fact, specific. Data in an example of this specification also demonstrate that the *C. viscosum* lipase is specific.

Immobilized non-specific lipase is disclosed in Y. Kimura et al., Eur. J. Microbiol. Biotechnol. 17 (1983), 107–112. The lipase is derived from *Candida cylindracea*, and the data in the article show that the immobilized lipase has optimum temperature about 40° C., and that there is significant deactivation at 50° C.

Immobilized non-specific lipase and its use for random interesterification of fat are described in Macrae, A. R. (1983), Journal of the American Oil Chemists' Society (JAOCS), 60, 291. However, the process temperature was only 40° C. This low temperature was probably chosen due to the poor thermostability of the *Candida cylindracea* lipase.

There is a need for thermostable, non-specific lipase for processing high-melting substrates at about 60° C. or higher without solvent, e.g. for randomization of fat in the margarine industry. Reference is made to A. R. Macrae and R. C. Hammond: "Present and Future Applications of Lipases", Biotechnology and Genetic Engineering Reviews, 3, 193–217 (1985). Prior-art preparations are not sufficiently heat-stable, and it is the object of the invention to provide non-specific lipase that is thermostable enough for long-term use at 60° C. or higher in soluble or immobilized form. The lipase should be microbial, as these can be produced economically.

STATEMENT OF THE INVENTION

We have found that a number of species belonging to the genus Candida produce novel non-specific lipases. Surprisingly, these novel lipases are more heat-stable in soluble and immobilized form than any previously known non-specific lipase, including those from *C. curvata* and *C. rugosa* (*C. cylindracea*).

Accordingly, the first aspect of the invention provides a positionally non-specific Candida lipase preparation, said preparation being characterized in that the residual lipase activity after 60 minutes incubation at 70° C. in 0.08 M citrate-phosphate buffer at pH 6.5 is above 10%, preferably above 50% and most preferably above 80%.

In the second aspect the invention provides a positionally non-specific lipase preparation, characterized in that the lipase activity after (a) 60 minutes at pH 6.5 and 60° C. followed by (b) 60 minutes at 65° C. in 0.1 M citratephosphate buffer at pH 6.5 is at least 20% of the activity remaining after (a).

In the third aspect the invention provides a positionally non-specific lipase preparation characterized by comprising a lipase derived from a strain of *C. antarctica*, *C. tsukubaensis*, *C. auriculariae*, *C. humicola* or *C. foliarum*, or a lipase showing immunochemical identity with such lipase and preferably also having same molecular weight as said lipase.

In the fourth aspect the invention provides a positionally non-specific lipase preparation, characterized by being obtainable by cultivation of a strain of *Candida antarctica, C. tsukubaensis, C. auriculariae, C. foliarum* or *C. humicola.*

In the fifth aspect the invention provides an immobilized non-specific lipase preparation obtained by immobilization of the aforesaid lipase.

In the sixth aspect the invention provides an immobilized non-specific Candida lipase preparation, with thermostability characterized in that the half-life of the lipase activity at 60° C. in continuous fixed-bed interesterification (preferably acidolysis) whereby the substrate is partly or fully saturated with water is above 1,000 hours.

In the seventh aspect the invention provides an immobilized non-specific Candida lipase preparation, with thermostability characterized in that the residual lipase activity after 72 hours incubation at 80° C. in triolein is above 10%, most preferably above 50%.

The invention furthermore provides a process for the production of positionally non-specific lipase, characterized by comprising cultivation of a strain of *Candida antarctica, C. tsukubaensis, C. auriculariae, C. humicola* or *C. foliarum* under aerobic conditions in a nutrient medium containing assimilable sources of carbon, nitrogen and phosphorous, preferably followed by recovery of the lipase from the fermentation broth.

The invention also provides a method for producing non-specific Candida lipase comprising the steps of (a) providing a suitable recombinant DNA cloning vector comprising DNA-sequences encoding functions facilitating gene expression and a DNA-sequence encoding the Candida lipase;

(b) transforming a suitable host organism with the cloning vector from step (a); and (c) culturing the transformed host in a suitable culture medium and optionally recovering the lipase from the culture medium.

Finally, the invention provides use in a lipase-catalyzed process (i.e. hydrolysis. ester synthesis or interesterification) of the above lipase preparations or lipase produced by the above method.

DETAILED DESCRIPTION OF THE INVENTION

Microorganisms

Lipases according to the invention can be produced by cultivation of strains belonging to the genus Candida, particularly Candida Group I as defined by N. J. W. Kreger van Rij: The Yeasts, a Taxonomic Study third revised and enlarged edition, Elsevier, Amsterdam (1984). Group I includes the basidiomycetous anamorphs of Candida. Preferred species are *C. antarctica* (Goto et al.) Kurtzman et al., *C. tsukubaensis, C. auriculariae, C. humicola* or *C. foliarum*, as defined in the said book. It is noted that *C. antarctica* has also been described under the synonyms *Sporobolomyces antarcticus* Goto et al., *Sterigmatomyces aphidis* Henninger & Windisch and *Trichosporon oryzae* Ito et al., and that *C. auriculariae* has been described under the synonym *Torulopsis auriculariae.*

The preferred Candida strains are those that produce non-specific lipase which shows immunochemical identity to one or more of the lipases exemplified hereinafter.

The preferred strains include the following three strains of *C. antarctica*, which have been deposited at Deutsche Sammlung von Mikroorganismen (DSM) under the terms of the Budapest Treaty:

| Deposit No. | Deposit date |
| --- | --- |
| DSM 3855 | 29 Sep 1986 |
| DSM 3908 | 8 Dec 1986 |
| DSM 3909 | 8 Dec 1986 |

The preferred strains also include the following strains, which are freely available to the public from Centralbureau voor Schimmelculturen (CBS), American Type Culture Collection (ATCC), Agricultural Research Culture Collection (NRRL) and Institute of Fermentation, Osaka (IFO) under the indicated deposit numbers:

*C. antarctica*: CBS 5955, ATCC 34888, NRRL Y-8295 (type strain)

*C. antarctica*: CBS 6678, ATCC 28323

*C. antarctica*: CBS 6821, NRRL Y-7954, ATCC 32657

*C. tsukubaensis*: CBS 6389, IFO 1940, ATCC 24555, NRRL Y-7792 (type strain)

*C. auriculariae*: CBS 6379, ATCC 24121, IFO 1580 (type strain)

*C. humicola*: CBS 571, ATCC 14438, IFO 0760 (type strain)

*C. humicola*: CBS 2041, ATCC 9949, NRRL Y-1266, IFO 0753

*C. humicola*: IFO 1527

*C. foliarum*: CBS 5234, ATCC 18820 (type strain)

As indicated above type strains of all five preferred Candida species were found to be productive of lipase of the invention.

Use of mutants and variants of the above-mentioned strains is also considered to be within the scope of the invention.

Genetic engineering techniques known in the art may be used to transfer the ability to produce lipase of the invention into other microbial strains. Use of such strains is also considered to be within the scope of the invention.

Thermostability

The lipases of the invention have good thermostability in soluble and immobilized form. Lipases of *C. antarctica, C. auriculariae* and *C. tsukubaensis* are preferred, and lipases derived from *C. antarctica* are particularly preferred, due to their thermostability.

For some lipase preparations according to the invention it is observed that during heat treatment they initially lose activity fairly rapidly, but the activity remaining after a certain time is very stable towards further heat treatment. This behavior may be due to the presence of two or more lipases of different thermostability, and/or to the presence of heat-labile protease and/or presence of a limited amount of lipase stabilizing components.

Heat-treatment of *C. antarctica* lipase, e.g. 1-3 hours at 60° C., results in a particularly thermostable lipase preparation.

Lipase production by cultivation of Candida

The Candida strains used in this invention may be cultivated under aerobic conditions in a nutrient medium containing assimilable carbon and nitrogen sources together with other essential nutrients, the medium being composed in accordance with principles known in the art.

Suitable carbon sources may be carbohydrates, lipids and other esters. Suitable nitrogen sources may be inorganic (e.g. nitrate or ammonium salts) or organic (e.g. yeast extract, corn steep liquor, soy bean meal, cotton seed meal or corn gluten).

pH of the medium may be 3.5-9.5, preferably 5.5-8.5. Fermentation temperature may be 15°-40° C., preferably 20°-34° C.

After fermentation, liquid enzyme concentrates may be produced by removal of coarse material from the broth and, if desired, concentration by evaporation or by reverse osmosis. finally, perservatives may be added to the concentrate.

Solid enzyme preparations may be prepared from the purified and/or concentrated broth by precipitation with salts, such as $Na_2SO_4$ or with water miscible solvents, such as ethanol or acetone; removal of the water in the broth by suitable drying methods such as spray-drying may also be employed.

Derivatized (chemically modified) lipase may be prepared by any method known in the art. One example is the polyethylene-glycol (PEG) modification described in Matsushima A. et al. (1986), Biotechnology Letters, 8, 72-78.

Constituent lipases A and B

It has been found that C. antarctica lipase contains two constituent lipases A and B. The properties and uses of each will be discussed later in this specification.

Purified lipase A and B may be produced from lipase after fermentation, e.g. by gel filtration.

Alternatively, recombinant DNA technology can be used to selectively transfer the gene coding for lipase A or B. A preferred method for this will be described below.

Lipase A is the more thermostable, and lipase B is more alkali-resistant than A, so treatment at high temperature or high pH can be used obtain a preparation containing mainly lipase A or B, respectively.

Lipases A has a molecular weight of 43 kD and an isoelectric point of 8.0±0.2. Lipase B has MW of 33 kD and pI of 6.0±0.2.

Immunochemical characterization of lipases

The preferred lipases of the invention show immunological identity with a lipase from one of the above-mentioned Candida species, particularly from one of the above-mentioned strains, and especially lipase A or B from DSM 3855.

The most preferred lipases have both immunological identity and identical molecular weight with one of these lipases.

Production of antiserum for use in immunological tests is described in Chapter 41 of N. H. Axelsen: Handbook of Immunoprecipitation-in-Gel Techniques (Blackwell Scientific Publications, 1983).

Immunological identity and molecular weight of proteins can be determined by SDS-polyacrylamide gel electrophoresis (SDS-PAGE) (e.g. according to Novo Analysis method AF 217-GB) followed by immunoblotting according to J. Hald et al., Journal of Reproductive Immunology, vol. 10, pp. 15-26 (1987).

Monospecific rabbit antiserum raised against purified lipase A from DSM 3855 (from Example 7) was used for immunoblotting of SDS-PAGE by the above-mentioned method to examine the following lipases:

C. antarctica: 0.2 OU solution of powder produced as in Example 3

C. tsukubaensis: 0.2 OU solution of the powder from Example 5

C. auriculariae: 0.1 OU solution of the powder from Example 6

C. humicola: 0.75% solution of the powder from Example 6B

C. foliarum: 3% solution of the powder from Example 6A

The C. antarctica lipase showed a strong band, and the C. tsukubaensis and C. humicola lipases showed weak bands, at the 43 kD position, i.e. they produce a lipase that is immunologically identical with lipase A from C. antarctica and has the same molecular weight. No band was observed for the C. auriculariae and C. foliarum lipase.

The identity tests may also be performed by the well-known Ouchterlony double immunodiffusion procedure or by tandem crossed immunoelectrophoresis according to Chapter 5 and 14 of the above-mentioned book by N. H. Axelsen.

Lipase production by recombinant DNA techniques

Recombinant DNA techniques may be used in order to obtain a higher yield of lipase or in order to produce a single constituent lipase, such as lipase A or B from C. antarctica described above, in good yield.

A preferred method uses an Aspergillus strain as the host and comprises the following steps:

(a) providing a suitable recombinant DNA cloning vector comprising DNA-sequences encoding functions facilitating gene expression and a DNA-sequence encoding the Candida lipase;

(b) transforming a suitable host organism with the cloning vector from step (a); and (c) culturing the transformed host in a suitable culture medium and optionally recovering the lipase from the culture medium.

It is especially preferred to use A. oryzae as the host according to EP 0,238,023, incorporated herein by reference.

Immobilized lipase

For the practice of this invention, lipase may be immobilized by any method known in the art, e.g. in K. Mosbach (ed.): Methods in Enzymology, 44, "Immobilized Enzymes", (Academic Press, New York, 1976). Available methods for enzyme immobilization include: cross-linking of cell homogenates, covalent coupling to insoluble inorganic or organic carriers, entrapment in gels and adsorption on ion-exchange resins or other adsorbent materials. Also, coating on a particulate support may be used, as described in Macrae A. R. and Hammond R. C. (1985), Biotechnology and Genetic Engineering Reviews, 3, 193.

A preferred immobilization method uses a particulate, macroporous resin. The lipase may be simply adsorbed on the resin, or it may be attached to the resin by cross-linking with glutaraldehyde or other cross-linking agent known in the art.

A preferred resin type is weakly basic anion exchange resin, e.g. of acrylic, polystyrene or phenolformaldehyde type. Examples of commercial products are Lewatit ® E 1999/85 (product of Bayer, West Germany) and Duolite ® ES-568 (Rohm & Haas). The immobilization on this type of resin is preferably according to EP 140 542, incorporated herein by reference.

Another preferred resin type is an adsorbent resin of the phenol-formaldehyde type. The immobilization on this resin is preferably done according to DK 85/878, incorporated herein by reference.

Yet another preferred resin type is adsorbent resin of the acrylic type. An example of a commercial product is Lewatit ® E2001/85 (product of Bayer).

Another preferred immobilization method uses an inorganic support material, and the lipase is preferably attached to the support by adsorption or covalent coupling. Such support materials and immobilization techniques are described in K. Mosbach (ed.): Methods in Enzymology, 44, "Immobilized Enzymes" (Academic Press, 1976).

Lipase-catalyzed processes

The lipases of the invention may be used in any of the following processes (reactants indicated in parenthesis):
Ester hydrolysis (ester+water)
Ester synthesis (acid+alcohol)
Interesterification, including.
  Acidolysis (ester+acid)
  Alcoholysis (ester+alcohol)
  Ester interchange or transesterification (ester+ester)
The alcohol may be mono- or polyvalent primary and/or secondary alcohol or a mixture of these. The acid may be any carboxylic acid or a mixture of these. The ester may be any ester derived from the mentioned alcohol and acid, or a mixture of these. Some advantageous process embodiments are described below.

Ester hydrolysis process

This may be performed either batch-wise or continuously. In a batch reactor the fat and water are mixed mechanically together with the necessary amount of lipase. Reaction time depends on enzyme dosage and desired conversion, but is generally from 4-6 hours up to 3-4 days. If an immobilized lipase is used it may be recovered at the end of reaction and reused, thereby improving process economy.

In a continuous process, fat above its melting point is passed through a reactor in which the immobilized lipase is retained. Water may be added to the system in several ways, e.g. by dispersing water in the fat or by intermittently absorbing water in the immobilized lipase.

For reasons of economy in recovery, the water content will usually be kept below 40% w/w. The temperature should be above the melting point of the reaction mixture, and may be as high as 80° C. Preferred temperatures are 45°-70° C.

An example of this process is fat splitting. If a high degree of hydrolysis is desired, it is preferable to use *C. antarctica* containing both lipase A and lipase B.

A second example of this process is hydrolysis of cholesterol esters.

As third example, fat containing high amounts of oleic acid or linolic acid may be hydrolyzed with *C. antarctica* lipase, preferably lipase A. The saturated fatty acids are hydrolyzed but oleic and linoleic acid are largely left untouched. After removal of free fatty acid, near-complete hydrolysis may be carried out chemically or enzymatically, e.g. with *C. antarctica* lipase B. After separation, fatty acid with a high content of oleic or linolic acid is obtained. By this process, oleic acid may be obtained from olive oil, and linolic acid may be obtained from cotton seed oil, soy bean oil or sunflower oil.

Ester synthesis process

The process of this invention is particularly advantageous for the synthesis of esters of secondary alcohols that are otherwise difficult to produce, including those where the acid or alcohol is high-melting.

The process may be performed batch-wise or continuously. In the batch process, the immobilized lipase may be recovered and reused to improve economy. Preferably, water is removed during reaction, e.g. by vacuum distillation or by absorption on molecular sieves. The temperature should be such that the reaction mixture is liquid, preferably 60°-90° C., more preferably 60°-80° C.

For ester synthesis from short-chain alcohols (primary or secondary) it is preferred to use *C. antarctica* lipase containing lipase B. For ester synthesis from long-chain, non-volatile alcohols, it is preferred to use a *C. antarctica* preparation containing lipase A, and to apply vacuum for water removal.

Ester interchange

In this process an organic solvent such as hexane or other hydrocarbons may be included in the reactant mixture. But due to the excellent thermostability of the lipases of this invention it will in most cases be possible and preferable to run the process in melted substrate without a solvent.

The reactant mixture may also include a small amount of water, in order to maintain the activity of the enzyme. Water content up to saturation may be used, but a high water content leads to an undesired high degree of by-product formation by hydrolysis.

Depending on the purity of reactants, purification may be needed prior to carrying out the reaction in order to achieve the highest productivity of the immobilized lipase. Conventional purification methods may be used, such as bleaching, alkali refining and deodorization.

Due to the excellent thermostability of the lipase, reaction temperature may be as high as 90° C. The lower limit for reaction temperature is determined by the melting point and viscosity of the reactant mixture. Preferred temperatures are from 60° to 90° C., most preferably from 60° to 80° C.

Immobilized lipase is highly preferred for ester interchange for reasons of convenience and economy. *C. antarctica* lipase containing component A is preferred. The reaction may be performed batch-wise or continuously.

In the batch process the substrate and if convenient solvent is mixed in a batch reactor which is heated to the preferred temperature together with the immobilized lipase. The substrate can be partly or fully saturated with water. The enzyme dosage can be up to 10% depending on the desired conversion and reaction time. The reaction time can be from a few hours to several days. After reaction the enzyme can be filtered off and reused, if convenient after a solvent wash.

In the continuous process the substrate is passed through a column containing the immobilized lipase. The substrate can be partly or fully saturated with water before entering the enzyme column. This can e.g. be done by a precolumn containing water saturated resin or by saturating the substrate in the substrate container. The desired conversion can be achieved by adjusting the flow rate through the column, i.e. changing the residence time.

The operation time in such a system can be up to several thousand hours. The slow loss of activity occurring can be compensated for by decreasing the flow rate, i.e. increasing the residence time of the reactant mixture. The initial residence time will depend on desired conversion and can typically be from 5 min up to 2 hours.

Examples of this process are fat randomization and production of glyceride of poly-unsaturated fatty acid.

Randomization of fat

A preferred embodiment of this process is random interesterification of fat, where the reactant mixture comprises triglyceride fat, and reaction occurs by exchange of acyl groups between triglyceride molecules.

The reactant mixture may consist of a single fat fraction, whereby exchange between acyl groups in the three different positions occurs.

The reactant mixture may also consist of two or more types of fat, especially one being liquid at ambient temperature and one being a high-melting fat. The latter may be obtained by fractionation from natural sources or by hydrogenation. The product obtained by randomization of such mixtures is useful in margarine production.

In another preferred embodiment of the ester interchange process, the reactants comprise a triglyceride fat and a carboxyl acid ester, especially a methyl or ethyl ester.

After the interesterification, the products may be further processed. By-products such as free fatty acids may be removed afterwards by conventional methods such as caustic refining.

The product itself can be fractionated, blended with other oils or similar, depending on the specific application.

Glyceride of poly-unsaturated fatty acid

Lipase of the invention may advantageously be used in acidolysis or ester interchange of fat and fatty acids or esters (especially methyl or ethyl esters), having a high content of poly-unsaturated fatty acids (PUFA) to produce fat with high PUFA content for dietary use. *C. antarctica* lipase is particularly suited for this as it has high activity for interesterifying PUFA.

EXEMPLARY PRACTICE OF THE INVENTION

Figure 1:
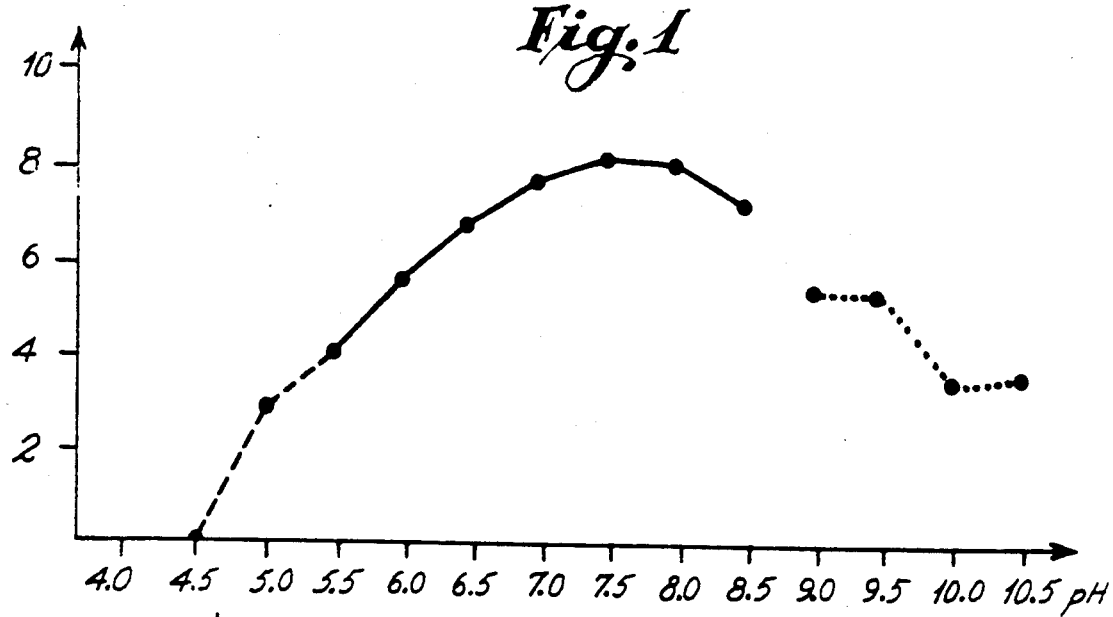
FIGS. 1, 2 and 3 show pH-activity curves for lipases of *C. antarctica*, *C. tsukubaensis* and *C. auriculariae*, respectively. Details are given in Example 14.

Assays for activity of soluble lipase (LU and OU)

Two methods are used. The first method is based on hydrolysis of tributyrine in a pH-stat. 1 LU (Lipase Unit) is the amount of enzyme which liberates 1 $\mu$mol titratable butyric acid per minute at 30° C., pH 7.0 with gum arabic as an emulsifier. Further details are given in Novo Analytical Method AF 95/5, available on request.

Measurement of activity in lipase units by hydrolysis of olive oil (OU) is carried out as follows: 1 ml enzyme solution, 5 ml emulsion (25 ml olive oil and 75 ml 2% polyvinyl alcohol, MW approx. 72,000 emulsified in a Waring blender), and 5 ml buffer (50 mM tris-maleate buffer pH 7.0) are mixed and incubated in a shaking water bath at 40° C. for 10 minutes. The reaction is stopped by addition of 20 ml stop reagent (500 ml acetone, 500 ml ethanol and 11 ml 1 N NaOH). The sample and a blank sample (stop reagent added before the emulsion) are titrated to pH 9.2 with 0.05 N NaOH. The activity (OU) is calculated from the difference in titrated NaOH between the sample and the blank, and is expressed as 1 $\mu$m liberated free fatty acid per min.

Non-specificity of soluble lipase

This may be determined by short-time hydrolysis of triglyceride and analysis of the resulting diglycerides (DG). A specific lipase will produce almost exclusively 1,2-DG, whereas a non-specific lipase will yield a significant content of 1,3-DG in the DG fraction. Hydrolysis and handling time must be kept short to avoid acyl migration.

More specifically the measurement is carried out as follows: 250 $\mu$l enzyme solution (4-100 OU/ml), 250 $\mu$l Trismaleate buffer, pH 7.0, and 500 $\mu$l substrate (triolein: 2%-polyvinyl alcohol, MW 72,000; 1:3) are mixed in an Eppendorf centrifuge-tube and shaken for 30-90 min at 42° C. The reaction is stopped by mixing with 10 ml CHCl$_3$ (0.2% lithocholic acid can be used as internal standard). The CHCl$_3$ is dried by Na$_2$SO$_4$. 1 $\mu$l is spotted on a thin layer chromatography rod (Chromarod Type S II, Newman-Howell Associates Ltd) and developed for 20 min with hexan/ether/acetic acid (70:30:1) as solvent. The partial glycerides are quantified by a FID analyser (Iatroscan TH 10, Newman-Howell Associates Ltd). Results are reported as 1,3-DG in % of total DG. Thus, a specific lipase would give 0, and a fully non-specific lipase would be expected to give around 33%.

Acidolysis activity of immobilized lipase (BIU, BIU-2)

The activity is determined by reacting palmitic acid with triolein with or without solvent. Total incorporation of palmitic acid is measured by FAME-GLC of triglyceride. Incorporation in the 2-position is measured by treating the triglycerides with pancreatic lipase to hydrolyze the 1- and 3-positions, and then analyzing the resulting 2-monoglyceride by FAME-GLC.

FAME-GLC (Fatty acid methyl ester - gas-liquid chromatography) may be done according to methods Ce 2-66 and Ce 1-62 published by the American Oil Chemists' Society (AOCS).

In case of reaction with solvent, the reaction mixture consists of 0.6 g of triolein, 0.174 g of palmitic acid and 8.083 g of petroleum ether. For reaction without solvent, 3.0 g of triolein and 0.87 g of palmitic acid is used.

In either case, a suitable amount of enzyme is hydrated, incubated with the above reaction mixture at a given temperature for 1–4 hours, and then filtering to stop the reaction. The filtrate is purified on an alumina column, and the triglycerides are analyzed by FAME-GLC.

Separately, triglycerides from 2 ml of the filtrate are purified in the same manner on 4 g of activated alumina. The approx. 100 mg triglycerides, 3 ml pancreatic lipase solution (250 mg porcine pancreas lipase grad II from Sigma cat. no. L3126 dissolved in 10 ml 1M trisbuffer pH 8), 300 µl 2M $CaCl_2$, and 0.75 ml 0.2% w/v taurocholate are mixed. The emulsion is heated in a water bath at 40° C. for 2 minutes and mixed on a Whirley mixer for 1½ minute before the reacton is stopped by addition of 4 ml 96% ethanol. The sample is transferred to a separation funnel and extracted with 4×20 ml diethyl ether. The ether phase is washed 4 times with 20 ml deionized water before it is dried by a $Na_2SO_4$ filter and evaporated. The sample is redissolved in 1 ml 1,1,1-trichloroethane. The glycerides are separated by preparative TLC on precoated TLC Plates silica gel 60 from Merck (activated 30 minutes at 110° C.) in a well saturated developing tank with diethylether and n-hexane (70:30) as a developing solvent. The TLC is run for 40 minutes at 20° C.

The monoglyceride band is identified by iodine vapour, scraped off and extracted by 3 times 10 ml diethyl ether. The ether fase is filtered, evaporated and the sample is methylated and analysed by GLC.

One BIU (Batch Interesterification Unit) is the amount of immobilized lipase that incorporates palmitic acid at an initial rate of 1 µmole/minute at the given temperature with or without solvent. One BIU-2 (BIU in 2-position) is defined similarly from incorporation in 2-position.

Transesterification activity of immobilized lipase (BTU)

The activity is determined by reacting an equimolar mixture of triolein and tripalmitin. Formation of mixed triglycerides (POO, PPO etc.) is measured by high-performance liquid chromatography (HPLC).

More specifically, 0.8855 g of triolein (OOO) and 0.8073 g of tripalmitin (PPP) (1 mM of each) are melted, and 250 mg of dry matter enzyme moisturized to 10% w/w water are added. The samples are shaken in a water bath for 15 minutes at a given temperature, and then analysed by HPLC.

HPLC may be done according to G. W. Jensen, J. Chromatogr., 204, 407 (1981).

One BTU (Batch Transesterification Unit) is defined as the amount of immobilized lipase that produces mixed triglyceride at an initial rate of 1 µmole/minute at the given temperature.

Non-Specificity Index of immobilized lipase ($NSI_1$, $NSI_2$)

This is best determined by interesterification (e.g. acidolysis) Measurement of exchange in the 2-position indicates the non-specificity. Two such methods are used here: the $NSI_1$ method with triolein and palmitic acid and the $NSI_2$ method with XOX triglyceride (X=palmitic/stearic acid, O=oleic acid) and lauric acid. The best method is $NSI_1$, but the analysis is very cumbersome. The $NSI_2$ method is easier to perform, but the result is influenced by the fatty acid specificity of the lipase. The two acidolysis methods are less prone to error due to acyl migration than the hydrolysis method used for soluble lipase.

In the $NSI_1$ method, BIU and BIU-2 are measured, and an index is calculated as $NSI_1 = 3 \times BIU\text{-}2/BIU$. This will be 0 for a completely specific lipase, and will be 1 for a non-specific lipase that reacts equally with all three positions.

In the NSI method, immobilized lipase is hydrated as required for activation usually to about 10% of water. The following mixture is used:
345 mg cocoa butter stearin. (Supplied by Aarhus Olie A/S, Denmark, and containing about 95% of XOX triglycerides)
480 mg of lauric acid (Merck), 99% pure
8.1 g of petroleum ether (BDH), boiling point 80°–100° C.
250 mg (as dry matter) of the immobilized lipase A mixture of the above ingredient is incubated in a shaking water bath for a time and temperature (in the range 40°–60° C.) as needed to obtain a suitable conversion. Pure triglycerides are then isolated by alumina chromatography, and fatty acid composition is determined by FAME-GLC.

An index is defined as follows:

$$NSI_2 = 3 \times (olefin\ decrease)/(lauric\ incorporated)$$

To distinguish between specific and non-specific lipase, a lauric acid incorporation in the range 30–65% is considered most suitable.

Culture media

Media with the following compositions were used in the examples. Each medium was autoclaved at 121°–130° C. for 20–90 minutes.

| Constituents (g/l) | Agar-3 | YeDP | YPG-agar | Bou-3 |
|---|---|---|---|---|
| Peptone | 6 | — | — | 6 |
| Trypsin digested casein | 4 | — | — | 4 |
| Yeast extract | 3 | 5 | 4 | 3 |
| Meat extract | 1.5 | — | — | 1.5 |
| Dextrose | 1 | 20 | 15 | 1 |
| Agar (Difco) | 24 | — | 20 | — |
| $K_2HPO_4$ | — | — | 1 | — |
| $MgSO_4.7H_2O$ | — | — | 0.5 | — |
| Polypeptone | — | 10 | — | — |

| Constituents (g/l) | Calc | Calc-2 | Ca4a | YS-4 | YS-25 |
|---|---|---|---|---|---|
| Pharmamedia | 40 | 40 | 40 | 20 | — |
| Yeast extract | 5 | 5 | 5 | 5 | 10 |
| Corn steep liquor | — | — | — | 40 | — |
| Dextrose | 3 | — | — | 3 | 5 |
| Sucrose | — | 3 | 5 | — | — |
| Soy bean oil (ml/l) | 30 | 30 | 30 | 30 | 20 |
| $K_2HPO_4$ | 5 | 5 | 5 | 5 | 5 |
| $MgSO_4.7H_2O$ | 1 | 1 | 1 | 1 | 1 |
| Peptone | — | — | — | — | 10 |
| Pluronic ® L61 (ml/l) | 0 | 0.86 | — | — | — |
| pH | 6.2 | 6.2 | 6.0 | 6.5 | 6.5 |

The composition of Pharmamedia is described in Traders' Guide to Fermentation Media Formulation, 1980, Traders' Oil Mill Co., pp. 50–51.

| Constituents (g/l)u | CG1g | CG4h | Ca19g |
|---|---|---|---|
| Pharmamedia | 20 | 40 | 40 |
| Yeast extract | 5 | — | — |
| Soy bean powder | 20 | — | — |
| Dextrose | 5 | 5 | — |
| Dextrin | — | — | 5 |
| Coconut oil | — | 5 | — |

-continued

| Constituents (g/l)u | CGlg | CG4h | Ca19g |
|---|---|---|---|
| Soy bean oil (ml/l) | 20 | — | 20 |
| Oleyl alcohol | — | — | 6 |
| $K_2HPO_4$ | 5 | 5 | 5 |
| $(NH_4)_2HPO_4$ | — | 5 | — |
| $MgSO_4.7H_2O$ | 1 | 1 | 1 |
| $NaNO_3$ | — | — | 2 |
| Thiamine, HCl (mg/l) | 10 | — | 10 |
| Trace elements (Difco manual) (ml/l) | 10 | 10 | 10 |
| Pluronic 60L (10%, ml/l) | 3 | 3 | 3 |
| Vitamin mixture (ml/l) | — | 3 | — |
| pH | — | — | 6.0 |
| Vitamin mixture: | | | |
| Biotin | | 2 mg/l | |
| Calcium pantothenate | | 400 - | |
| Inositol | | 2,000 - | |
| Nicotinic acid | | 400 - | |
| Thiamine, HCl | | 400 - | |
| Pyridoxine, HCl | | 400 - | |
| p-aminobenzoic acid | | 200 - | |
| Riboflavin | | 200 - | |
| Folic acid | | 10 - | |

EXAMPLE 1

Production of lipase from *C. antarctica*

A culture of *Candida antarctica* strain DSM 3855 on Agar-3 slants was transferred to a 2000 ml shake flask with 800 ml of Bou-3 medium, and shaken at 26° C. for one day (200 rpm, amplitude approx. 2 cm).

The resulting culture broth was used as seed culture for a 10 l conventional fermenter, with 7 liters Cale-2 medium.

Fermentation conditions were as follows: Fermenter type: Laboratory fermenter FL 110 from Biotec AB, Bromma, Sweden.

| Aeration: | 6 Nl/min |
|---|---|
| Agitation: | 520 rpm by an agitator with two impellers with six blades each |
| Temperature: | 26° C. |
| pH: | There was no pH control |
| Time: | 119 hours |

The lipase yield was 157 LU/ml

The culture broth from the fermenter was centrifuged for 35 minutes at 4100 rpm by means of a Sorvall RC-3B centrifuge with a 6000 A rotor. The supernatant (a total of 5 l) was concentrated by ultrafiltration (and washed 5 times with one volume water each) to 600 ml by a Pellicon ultrafiltration apparatus from Millipore with a 10,000 MW cut-off filter sheet. 600 ml 99% cold ethanol was added to 560 ml of the UF-concentrate and the mixture was stirred for 30 min at 4° C. followed by a centrifugation (as above). 2.5 vol cold 99% ethanol was then added to the supernatant from the first ethanol precipitation. The mixture was stirred for 30 minutes and centrifuged (as above). The pellet from this centrifugation was dissolved in approx. 230 ml water and freeze-dried to give 22 g powder of 16,200 LU/g.

The lipase was further purified by use of hydrophobic interaction chromatography with ethanol elution followed by vacuum drying to give a powder of approx 92,000 LU/g.

Reference Example 1

Preparation of *C. curvata* lipase

*Candida curvata* strain CBS 570 (alias ATCC 10567) was used. CBS indicates Centraalbureau voor Schimmelcultures, Baarn, Netherlands, and ATCC indicates American Type Culture Collection, Rockville, Md., USA. A culture of this strain on an Agar-3 slant (see Example 1) was transferred to four 500 ml shake flasks with 100 ml Bou-3 medium (see example 1) each, and shaken at 26° C. for 1 day (200 rpm, amplitude approx 2 cm)

The culture broth of the Bou-3 shake flasks was used as a seed culture for inoculating two hundred 500 ml shake flasks, each with 200 ml LR-15 medium:

The composition of LR-15 medium was as follows:

| Constituent | Concentration |
|---|---|
| Pharmamedia | 50 g/l |
| $K_2HPO_4$ | 5 - |
| $NaNO_3$ | 1 - |
| $MgSO_4.7H_2O$ | 0.5 - |
| Tween-80 | 20 - | pH adjusted to 7.0 by HCl
Autoclaved at 121° C. for 40 minutes.
Tween-80 is Polyoxyethylene sorbitan monooleate (obtained from Merck).

Each shake flask was inoculated with 0.5-2 ml of Bou-3 culture broth and shaken with 200-300 rpm (amplitude approx. 2 cm) at 26° C. for 4 days.

The culture broth from the shake flasks was pooled at harvest giving rise to 29.5 l in total with a lipase activity of 15 LU/ml. The broth was centrifuged as described in Example 1, followed by a concentration also as described in Example 1, but only washed twice with 1 volume water, giving 3.9 l concentrate with a lipase activity of 168 LU/ml.

EXAMPLE 2

Production of lipase from *C. antarctica* in pilot plant

A culture of *Candida antarctica* strain DSM 3855 was inoculated on a Fernbach flask containing YPG-agar The Fernbach flask was incubated for 8 days at 26° C. before it was used to inoculate a conventional agitated and aerated seed fermenter containing 300 liter medium with the following composition:

| Yeast extract | 3.0 kg |
|---|---|
| $KH_2PO_4$ | 0.2 - |
| $Na_2HPO_4.12H_2O$ | 0.2 - |
| Glucose | 0.3 - |
| Pluronic 60 L | 125 ml |
| pH | 5.6 |

After 1 day's fermentation at 26° C. the broth was used to inoculate a conventional agitated and aerated fermenter with 1500 liter medium with the following composition:

| Yeast extract | 7.0 kg |
|---|---|
| Pharmamedia | 56.0 - |
| $KH_2PO_4$ | 4.0 - |
| $Na_2HPO_4.12H_2O$ | 3.0 - |
| Sucrose | 4.2 - |
| $MgSO_4.7H_2O$ | 1.4 - |
| Soy bean oil | 42 l |

|  |  |
| --- | --- |
| -continued | |
| Pluronic 60 L | 600 ml |
| pH | 6.2 |

The fermentation was run for 5 days at 26° C. with 1000 Nl/min aeration and 200 rpm agitation. The yield was 82 LU/ml.

The lipase was recovered by the following procedure: 1) drum filtration of the culture broth, 2) clear filtration, 3) concentration by ultrafiltration, 4) addition of ethanol to 50% w/w, 5) clear filtration, 6) concentration by ultrafiltration, 7) addition of ethanol to 77% w/w, 8) centrifugation, 9) vacuum drying, 10) redissolving in water, 11) batch hydrophobic interaction purification (the lipase was absorbed on a hydrophobic matrix, washed with water and eluted with 50% w/w ethanol), and 12) evaporation of the ethanol and freeze drying. The resulting powder had an activity of 143,000 LU/g.

EXAMPLE 3

Production of *C. antarctica* lipase powder

*Candida antarctica* culture DSM 3855 was maintained on PDA-agar slants.

| Composition of PDA-agar: | |
| --- | --- |
| Bacto potato dextrose agar (Difco) | 39 g/l |
| Agar | 10 - |

Autoclaved at 121° C. for 20 minutes.

50 shake flasks with medium Ca1e were inoculated from agar slants and cultivated at 25° C. for 64 hours.

The broth (46 OU/ml) was centrifugated at maximum 4,400 g for 20 minutes. The supernatant was concentrated to 1 liter and desalted with 1 liter water on an Amicon ultrafiltration apparatus with a H1P 10-20 cartridge (cut-off 10,000 MW) and freeze dried. The activity of the powder was 4000 OU/g.

EXAMPLE 4

Production of *C. antarctica* lipase

Cultures of strains DSM 3908 and DSM 3909, maintained on PDA-agar slants (see Example 3) were transferred to shake flasks containing YS-4, YS-25 or Ca4a medium, and cultivated for 2 or 3 days at 25° C. Lipase activity (OU) of the broth was measured.

|  | Strain | Results: Medium | Ferm. time | OU/ml |
| --- | --- | --- | --- | --- |
| 1. | DSM 3908 | YS-4 | 3 days | 8.5 |
| 2. | DSM 3908 | YS-25 | 2 - | 4.0 |
| 3. | DSM 3908 | Ca4a | 3 - | 26.0 |
| 4. | DSM 3909 | YS-4 | 3 - | 10.5 |
| 5. | DSM 3909 | YS-25 | 2 - | 5.0 |
| 6. | DSM 3909 | Ca4a | 2 - | 23.3 |

EXAMPLE 5

Production of *C. tsukubaensis* lipase

The *Candida tsukubaensis* culture CBS 6389 was maintained on PDA-agar slants (composition of PDA-agar are given in Example 3).

Two YeDP shake flasks were inoculated and cultivated for 24 hours at 25° C.

This culture was used to inoculate 52 shake flasks with CG-1g medium.

The shake flasks were cultivated for 4 days at 25° C. The broth were centrifugated at maximum 4,400 g for 20 minutes. The supernatant (3 l) was concentrated to 450 ml and desalted with 2 liter water on an Amicon ultraconcentration apparatus with a H1P 10-20 cartridge and freeze dried to give 24 g powder with 223 OU/g, 135 LU/g.

EXAMPLE 6

Production of *C. auriculariae* lipase

The *Candida auriculariae* culture CBS 6379 was maintained on PDA-agar slants.

70 CG4h shake flasks were inoculated from agar slants and cultivated at 25° C. for 4 days.

The broth was centrifugated at max. 4,400 g for 20 minutes and max. 12,200 g for 10 minutes. The supernatant was concentrated from 5.5 l to 950 ml on an Amicon ultrafiltration apparatus with a H1P 10-20 cartridge and freeze dried to give 29,1 g powder with 93 OU/g and 3.4 LU/g.

EXAMPLE 7

Production of *C. foliarum* lipase

A culture of CBS 5234 was maintained on PDA-agar slants. 60 shake flasks, each containing 150 ml of CG4h medium, were inoculated from agar slants and were then cultivated for 4 days at 25° C.

The broth was centrifuged at 4,000 rpm for 25 minutes, and then at 10,000 rpm for 10 minutes. The supernatant was concentrated from 6 liters to 550 ml on an Amicon ultrafiltration apparatus (PIH 10-20), desalted with 1 liter of deionized water and then freeze dried to give 38.4 g of powder with activity 275 OU/g or 313 LU/g.

EXAMPLE 8

Preparation of *C. humicola* lipase

CBS 571 was cultured on PDA-agar slants for 4 days at 25° C. A seed culture of YePD medium (composition given in Example 5) was inoculated from the agar slants and was cultivated for 17 hours at 25° C. 39 shake flasks with YS-4 medium (see Example 4) were inoculated from the seed culture and were then cultivated for 4 days at 25° C.

The broth was centrifuged at 4,000 rpm for 15 minutes, and then at 12,000 rpm for 15 minutes. The supernatant (1,300 ml) was concentrated on Amicon PIH 10-20 and desalted with 4 liters of deionized water to a final volume of 200 ml. This was freeze-dried to give 10.4 g of powder with activity 2,000 OU/g.

EXAMPLE 9

Production of lipase from 5 Candida species

Each strain indicated below was inoculated on a PDA-agar slant (see Example 3) and cultivated for 3 days at 25° C. Cells were then suspended in 9 ml of sterile, deionized water and inoculated in YePD medium (see Example 5) as seed culture and cultivated for 17–23 hours. 2 to 7 ml of the culture broth was reinoculated in shake flask with Ca19g medium, YS-4 medium or YS-25 medium (see Example 4) and cultivated for 3 days at 25° C. with shaking. pH and lipase activity (OU) of the broth were then measured.

| | Species | Results: Strain No. | Medium | pH | OU/ml |
|---|---|---|---|---|---|
| 1. | C. antarctica | DSM 3855 | Ca19g | 7.0 | 27.8 |
| 2. | - - | CBS 5955 | Ca19g | 6.7 | 25.3 |
| 3. | - - | CBS 6678 | Ca19g | 6.6 | 25.3 |
| 4. | - - | CBS 6821 | Ca19g | 6.6 | 46.8 |
| 5. | C. tsukubaensis | CBS 6389 | Ca19g | 7.5 | 11.8 |
| 6. | - - | CBS 6389 | YS-4 | — | 11.8 |
| 7. | C. auriculariae | CBS 6379 | YS-4 | — | 0.8 |
| 8. | C. foliarum | CBS 5234 | Ca19g | 7.0 | 7.3 |
| 9. | C. humicola | CBS 2041 | Ca19g | 5.9 | 15.0 |
| 10. | - - | CBS 2041 | YS-4 | 7.7 | 20.5 |
| 11. | - - | CBS 571 | Ca19g | — | 10.8 |
| 12. | - - | CBS 571 | YS-4 | 7.2 | 38.8 |
| 13. | - - | IFO 1527 | Ca19g | — | 1.8 |

As reference, *C. curvata* CBS 570 was cultivated in the same way with 4 days cultivation in YS-25 medium. The activity was 34.8 OU/g.

EXAMPLE 10

Separation and characterization of constituent lipases A and B from *C. antarctica*

Partially purified lipases from *C. antarctica* obtained as in Example 2 were further purified as follows. 1 g of the enzyme powder was suspended in 50 mM Tris-acetate pH 6. 1 g of DEAE-sephadex A50 was swollen and washed in 50 mM Tris-acetate pH 6 and was added to the enzyme suspension. Mixture was stirred for one hour at room temperature and filtered on a sintered glass funnel. The filtrate was then concentrated by ultrafiltration and dialyzed against 20 mM citrate buffer pH 4.5 and applied on CM-sepharose column equilibrated with the same buffer. B-enzyme was eluted as effluent and A-enzyme was eluted with salt gradient.

Molecular weight or the A and B enzyme were determined by Pharmacia Phast ™ system using 8–25% SDS PAGE gradient gels. Molecular weight for A and B enzymes were found to be 43 and 33 kD, respectively. Isoelectric points for the A and B enzymes were determined by using LKB Ampholine page plate with pH range 3.5 to 9.5 pI for A enzyme was 8.0±0.2 and for B enzyme 6.0±0.2.

For further purification of B enzyme the pool obtained as effluent from CM-sepharose was dialyzed against 20 mM borate pH 10 and applied on Mono-Q ™ (Pharmacia) column equilibrated with the same buffer. Activity of the B-enzyme was eluted with salt gradient using pharmacia FPLC equipment.

pH stability of the enzyme

A and B enzymes were diluted in 20 mM phosphate buffer for pH 6 or 7 and 20 mM borate buffer pH 8, 9 or 10. Final enzyme concentration was adjusted to $OD_{280}=1$ and incubated for 1½ hour at room temperature and overnight at 4° C. The table below shows % residual activity measured by LU method. Activity of the enzymes at pH 7 was adjusted as 100%. It is seen that A-enzyme was totally inactive at pH 10 after overnight incubation at 4° C., whereas B-enzyme maintained more than 78% of its activity at pH 10, but was less stable at pH 6.

| Time of incubation | A-enzyme | | B-enzyme | |
|---|---|---|---|---|
| pH | 1½ h | 20 h | 1½ h | 20 h |
| 6 | 85 | 91 | 87 | 30 |
| 7 | 100 | 100 | 100 | 72 |
| 8 | 101 | 100 | 88 | 77 |
| 9 | 125 | 103 | 101 | 85.7 |
| 10 | 18 | 0 | 91 | 79 |

Effect of temperature on activity

Lipase activity was measured by the LU method, except that temperature was varied. Results are shown below, with activity at 30° C. taken as 100%.

| | % increase in activity | |
|---|---|---|
| Temperature | A-enzyme | B-enzyme |
| 30° C. | 100 | 100 |
| 40° C. | 128 | 103 |
| 50° C. | 160 | 119 |
| 60° C. | 169 | 112 |
| 70° C. | 192 | 116 |

Effect of pH on activity

Figure 4:
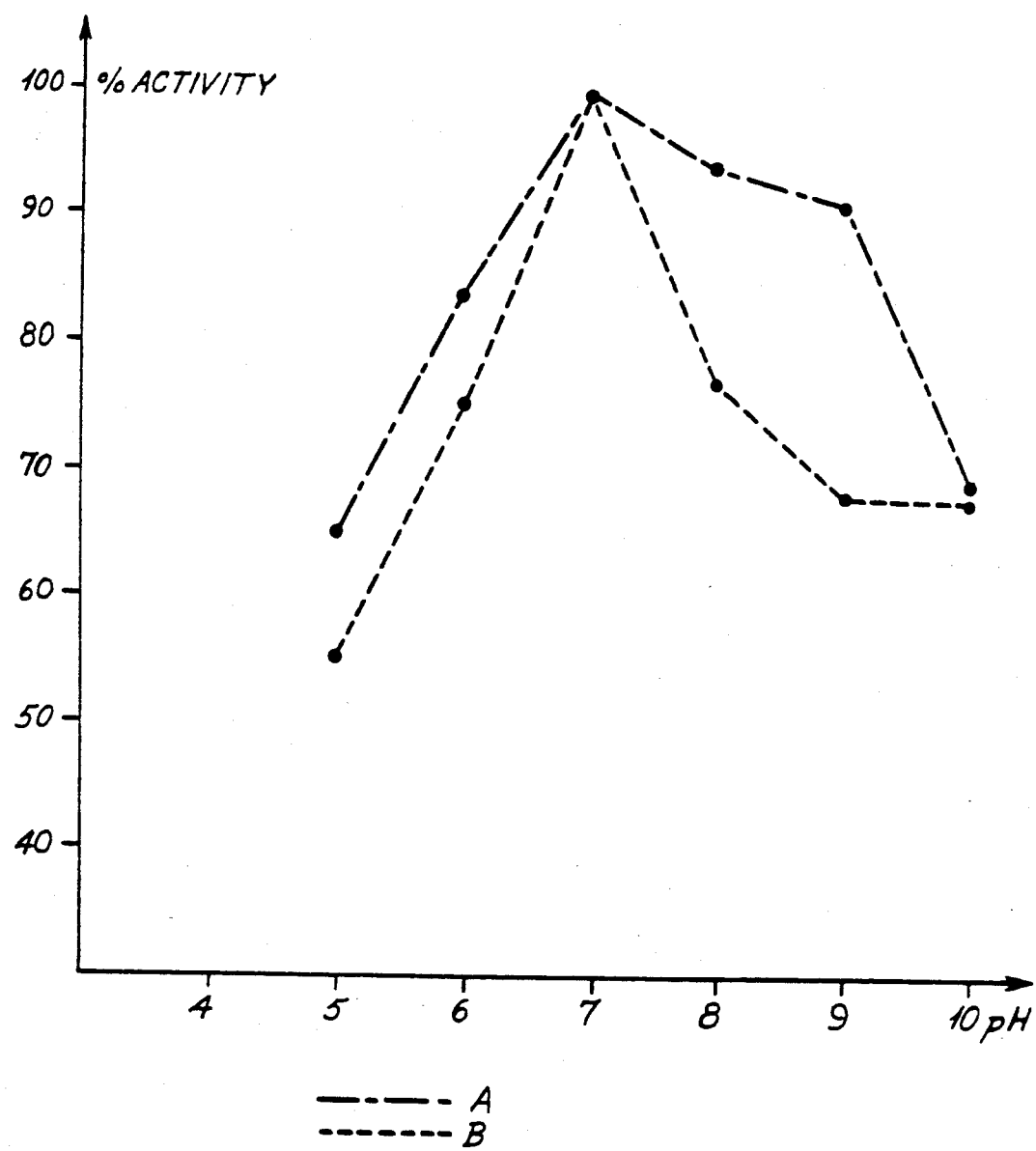
FIG. 4 shows the pH-activity curves for *C. antarctica* lipases A and B. Details are given in Example 10.

Lipase activity was measured by the LU method, except that pH was varied. Results obtained at respective pHs in the absence of the enzyme were used as controls for spontaneous hydrolysis. Results are shown in FIG. 4. It is seen that optimum pH for both A and B enzymes was found to be around pH 7.

EXAMPLE 11

Thermostability of lipases

Samples of culture broth prepared as in Example 9 (with Ca19g or YS-4 medium) were heat-treated for 30 minutes at 60°, 70° and 84° C. Lipase activity of the heat-treated samples and of a control sample without heat-treatment was then detected by applying the sample to a diffusion plate containing olive oil, polyvinyl alcohol (PVA) and brilliant green in agar at pH 5.5, and measuring the zone of color change (diameter in mm) after 24 hours diffusion at 30° C.

| | | Heat treatment | | | |
|---|---|---|---|---|---|
| Species | Strain No. | None | 60° C. | 70° C. | 84° C. |
| C. antarctica | CBS 5955 | 6.0 | 6.0 | 5.5 | 5.0 |
| C. foliarum | CBS 5234 | 6.0 | 6.5 | 6.5 | ND |
| C. humicola | CBS 2041 | 7.5 | 4.5 | 4.5 | 4.5 |
| - - | CBS 571 | 7.0 | 4.5 | 4.5 | 4.5 |
| - - | CBS 1527 | 7.0 | 4.5 | 4.5 | 4.5 |
| C. auriculariae | CBS 6379 | 6.0 | 6.0 | 0 | ND |
| C. curvata (reference) | | 9.5 | 0 | 0 | 0 |

It is seen that lipases from *C. antarctica* and *C. humicola* were stable up to 84° C., *C. foliorum* lipase up to 70° C., and *C. auriculariae* lipase up to 60° C., whereas the prior-art *C. curvata* was unstable at 60° C.

EXAMPLE 12

Thermostability of soluble lipases

The thermostabilities of the following lipases were compared.
Invention:

C. antarctica: A 0.8% solution of the powder from Example 1

Purified lipase A: The sample from Example 10 was dialysed overnight against 15 mM tris-maleate buffer pH 7.

Reference:

C. cylindracea: A 1% solution of Lipase OF obtained from Meito Sangyo

C. curvata: The UF-concentrate from reference Example 1

The following buffers were used in the experiment:

Tris-maleate buffer 0.1 M, pH 6.0:
  50 ml 0.1M tris (hydroxymethyl) aninomethane plus
  26 ml 0.1M maleic acid Citrate-phosphate buffer 0.1 M, pH 6.5:
  142 ml 0.05M citric acid plus
  355 ml 0.1M dibasic sodium phosphate ($Na_2HPO_4$)

Phosphate buffer 0.1 M, pH 7.5:
  16 ml 0.1M $NaH_2PO_4$ plus
  84 ml 0.1M $Na_2HPO_4$ The thermostability was measured by mixing 1 ml lipase solution with 4 ml of buffer in a test tube. The test tube was incubated for 60 minutes in a 60°, 65° or 70° C. water bath. The thermostability is expressed as residual activity (LU/ml) in percent of the activity (LU/ml) of the enzyme buffer mixture before incubation.

The results (residual activities) were as follows:

| Enzyme incubation temperature | INVENTION | | | | | | REFERENCE | | | | | |
|---|---|---|---|---|---|---|---|---|---|---|---|---|
| | C. antarctica | | | Lipase A | | | C. curvata | | | C. cylindracea | | |
| Buffer pH | 60° C. | 65° C. | 70° C. | 60° C. | 65° C. | 70° C. | 60° C. | 65° C. | 70° C. | 60° C. | 65° C. | 70° C. |
| 6.0 | | | | | | | 32% | 3.5% | 0.9% | | | |
| 6.5 | 82% | 78% | 83% | 98% | 95% | 93% | 10% | 0.9% | 0.9% | 1.1% | 1.1% | 0.6% |
| 7.5 | 29% | 18 | 8% | | | | 2.2% | 0.8% | 1.0% | 0.2% | 0.2% | 0.5% |

The pH 6 incubations for C. curvata with the tris-maleate buffer were included, as there were the conditions used by D. Montet et al. in their description of the lipase (Fette Seifen Anstrichmittel 1985, 87:181–185) and therefore considered to be suitable for this lipase.

It can be concluded that C. antarctica lipase and lipase A are far more thermostable than prior art C. cylindracea and C. curvata lipases.

EXAMPLE 13

Thermostability of lipases after heat-treatment

In this experiment, lipase samples were first pre-treated for 1 hour at 60° C., pH 6.5 as follows: Invention:

C. tsukubaensis: The powder from Example 5 was dissolved (7%) in pH 6.5 buffer (see above), and pre-treated for 1 hour at 60° C.

Purified lipase A: The eluate from the column (Example 10) was dialyzed overnight against 15 mM tris-maleate buffer pH 7, diluted 5 times with pH 6.5 buffer and pre-treated for 1 hour at 60° C.

Reference:

C. curvata: The UF-concentrate from ref. Example 1. The concentrate was adjusted to pH 6.5 and incubated for 1 hour at 60° C., pH 6.5. This pre-treated sample was diluted 5 times in buffer (pH 6, 6.5, 7.5, see above) for the thermostability experiments.

The above pre-treated samples were then incubated for 1 hour at 65° C. and pH 6.0, 6.5 or 7.5.

Results were as follows:

| Lipase | INVENTION | | REFERENCE | |
|---|---|---|---|---|
| | C. tsukubaensis | Purified lipase A | C. curvata | |
| Remaining activity after preheat treatment | 26% | 9% | 49% | |
| Incubation pH | 6.5 | 6.5 | 6.0 | 6.5 | 7.5 |
| Remaining activity after 1 hour at: 0° C. | 100% | 100% | 100% | 100% | 100% |
| 65° C. | 46,2% | 99% | 2,8% | 1,2% | 1,1% |

It is seen that the two lipases of the invention lose some activity during pre-treatment at 60° C., but the pre-treated samples are very stable at 65° C. The prior-art lipase from C. curvata is rapidly inactivated at 65° C.

EXAMPLE 14

Thermostability of C. antarctica lipase

Lipase powder obtained as in Example 3 was dissolved in water (1%), and further diluted 5 times in 50 mM tris-maleate buffer pH 7. This solution was pre-treated at 60° C. for 0, 60 and 180 minutes, and then heat treated for 30 minutes at various temperatures. Remaining activity after each step was measured by the OU method.

| Pre-treatment time at 60° C. | 0 min | 60 min | 180 min |
|---|---|---|---|
| Remaining activity after pre-treatment | 100% | 39% | — |
| Heat treatment 30 minutes, at | | | |
| 0° C. | 100% | 100% | 100% |
| 30° C. | 100% | 103% | 126% |
| 40° C. | 96% | 105% | 137% |
| 50° C. | 81% | 108% | 148% |
| 60° C. | 62% | 86% | 135% |
| 70° C. | 60% | 86% | 135% |
| 80° C. | 29% | 55% | 111% |

The results show that some lipase activity is lost during pre-treatment at 60° C., but the remaining lipase activity is extremely heat-stable, even at 80° C.

It is not clear why some data are considerably above 100%.

EXAMPLE 15

Activity vs. temperature for C. antarctica lipase

The enzyme activity of C. antarctica lipase (0.1% of the powder from Example 3) was measured at 30°, 40°, 50°, 60°, 65°, and 70° C. The activities were measured by the OU method described in the text, but with incubation at different temperatures. The results were as follows.

| Incubation temperature | 30 | 40 | 50 | 60 | 65 | 70 |
|---|---|---|---|---|---|---|
| Activity OU/ml | 2.1 | 2.3 | 3.4 | 5.2 | 6.3 | 5.8 |

EXAMPLE 16 pH-activity of lipases

The pH dependence of the activities of lipase from *C. antarctica* (0.2% solution of the powder from Example 3), *C. tsukubaensis* (3.0% solution of the powder from Example 5), *C. auriculariae* (3.0% solution of the powder from Example 6), *C. humicola* (Example 7) and *C. foliorum* (Example 8) were measured.

pH was varied from 4.0 to 10.5 in steps of 0.5 units. The buffers used were sodium acetate/acetic acid at pH 4.0-5.5 (200 mM for *C. antarctica* and 100 mM for the other lipases), 50 mM tris-maleate/NaOH at pH 5.5-8.5 and glycine/NaOH at pH 9.0-10.5 (200 mM for *C. antarctica* and 100 mM for the other lipases).

The measurements were carried ou as in the OU-method, but with 5 ml enzyme dissolved in buffer instead of 1 ml enzyme solution and 5 ml tris-maleate buffer.

Figure 2:
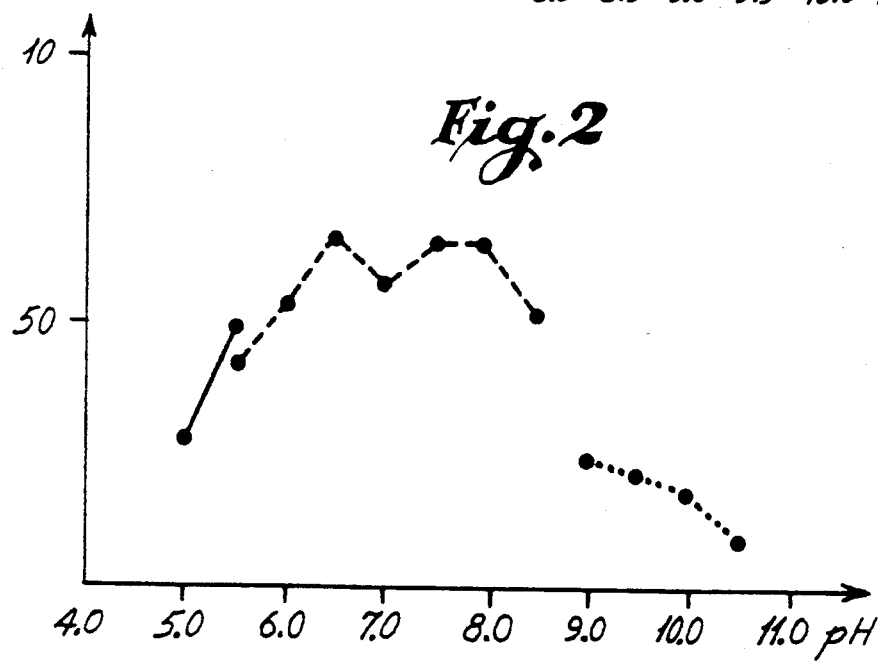
Figure 3:
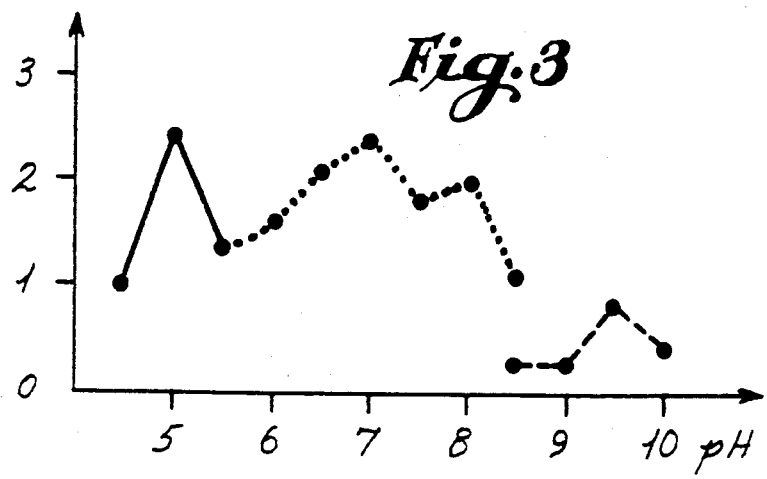

The pH-activity curves are shown in FIGS. 1, 2 and 3 for *C. antarctica, C. tsukubaensis* and *C. auriculariae,* respectively. The curves for *C. humicola* and *C. foliorum* lipases were similar. Thus, all lipases showed optimum around pH 7 to 8.

EXAMPLE 17

Non-specificity of soluble lipases

Culture broth prepared as in Example 9 was tested by the non-specificity method indicated previously. Results are given as 1,3-diglyceride in % of total diglyceride:

| Species | Strain no. | % 1.3-diglyceride |
|---|---|---|
| C. antarctica | CBS 6678 | 32% |
| C. humicola | CBS 2041 | 51% |
| C. tsukubaensis | CBS 6389 | 48% |
| C. foliorum | CBS 5234 | 45% |
| C. auriculariae | CBS 6379 | 50% |

Lipases from *Candida antarctica* (0.2% solution of a powder obtained as in Example 3), *C. tsukubaensis* (3.0% of the powder from Example 5), *C. auriculariae* (3.0% of the powder from Example 6) were measured by the same method.

| C. antarctica | 41% |
|---|---|
| C. tsukubaensis | 48% |
| C. auriculariae | 50% |

All the lipases are seen to be non-specific.

EXAMPLE 18

Substrate specificity of constituent *C. antarctica* lipases

The activities of purified lipases A and B (from Example 10) on various substrates were compared. Activities on tributyrine and olive oil were measured by the LU and OU methods, respectively. Activities on methyloleate, methyllaurate and racemic diolein were measured by the LU method with the following modifications: 1% substrate (methyllaurate 99% pure from Nu Check Prep, methyloleate 99% pure from Nu Check Prep, or racemic diolein 99% pure from Sigma) instead of tributyrine, and with NaOH titration at pH 8.5 instead of pH 7.0.

Below the results are presented as per cent activity relative to the tributyrine:

| Substrate | Lipase A | Lipase B |
|---|---|---|
| Tributyrine (LU) | 100% | 100% |
| Olive oil (OU) | 110% | 65% |
| Racemic diolein | 27% | 313% |
| Methyllaurate | 22% | 140% |
| Methyloleate | 8% | 60% |

It is seen that lipase B has high activity on diglycerides and methyl esters, whereas lipase A has relatively low activity to these, in relation to activity on triglyceride.

EXAMPLE 19

Immobilization of *C. antarctica* lipase on anion exchange resin 0 6 grams of *Candida antarctica* lipase obtained as described in Example 1 was diluted with water to 7.5 grams and mixed with 1.5 grams dry matter of Lewatit ® E1999/85 weakly basic anion exchange resin (product of Bayer) adjusted to pH 7.

The mixture was rotated during 24 hours at room temperature. After washing with water the preparation was dried in vacuum at room temperature giving 1.83 grams (dry matter content 98%). The activity remaining in the filtrate was 39% corresponding to a load of about 19,000 LU/g dry matter immobilized lipase.

EXAMPLE 20

Immobilization on anion exchange resin 12.5 ml lipase solution (12.500 LU/ml) of *C. antarctica* lipase obtained as in Example 2 and 4.25 g dry matter Duolite ® ES-568 weakly basic anion exchange resin (product of Rohm & Haas) adjusted to pH 7 were mixed and rotated for 24 hours at room temperature. After washing with water the preparation was dried in vacuum at room temperature, giving 4.6 g dry matter immobilized lipase. The activity remaining in the filtrate was 33%, corresponding to a load of about 22700 LU/g dry matter immobilized lipase. The activity was 9.2 BIU/g, measured by the previously indicated method

EXAMPLE 21

Immobilization on anion exchange resin 100 ml with 15,000 LU/ml *C. antarctica* lipase obtained as in Example 2 were mixed with 46 g dry weight of washed Lewatit ® E 1999/85 weakly basic anion exchange resin (product of Bayer) adjusted to pH 7. The mixture was stirred for 24 hours at room temperature. After washing with water the preparation was dried in vacuum at room temperature giving 51.5 g (dry matter content 99%). The activity remaining in the filtrate was 1% corresponding to a load of 29,200 LU/g. The activity was 37.6 BIU/g.

EXAMPLE 22

Immobilization on adsorbent resin 60 ml with 12,500 LU/ml *C. antarctica* lipase obtained as described in Example 2 were mixed with 25 g dry weight of washed Lewatit® E 2001/85 non-ionic resin (product of Bayer) adjusted to pH 7. The mixture was stirred for 24 hours at room temperature. After washing with water the preparation was dried in vacuum at room temperature giving 25 g (dry matter content 98%). The activity in the remaining filtrate was 1.6%, corresponding to a load of 30,200 LU/g.

EXAMPLE 23

Immobilization on adsorbent resin

The previous example was repeated, using 100 ml with 15,000 LU/ml *C. antarctica* lipase and 50 g of resin, giving 58 g (dry matter content 98%) the activity in the remaining filtrate was 2%, corresponding to a load of 25,800 LU/g. The activity was 52.2 BIU/g.

EXAMPLE 24

Immobilization of purified lipase A

Preparation of carrier: 10 g of Lewatit® 2001/85 were washed on a G-2 glass filter, the pH was adjusted to pH 7 by pH-stat using 0.05 N NaOH (2 hours' run), washed again, and dried on the glass filter. The dry matter was measured as 61.55%, and 2.5 g dry weight were used for the immobilization.

Preparation of the enzyme: Lipase A (Example 10) was dialyzed overnight against 15 mM Tris-maleate buffer pH 8, resulting in 15 ml of 8000 LU/ml.

Immobilization: Carrier and enzyme were mixed overnight, washed on a glass filter, and dried for 2 hours in vacuum. The dry matter was 96%. 2% of the activity remained in the solution, corresponding to a load of 28,200 LU/g.

EXAMPLE 25

Immobilization of purified lipase A

Carrier was prepared as in the previous example. The dry matter was measured as 76.32%, and 4.4 g dry weight were used for the immobilization.

Enzyme was prepared as in the previous example, resulting in 24.7 ml of 5400 LU/ml.

Immobilization: Carrier and enzyme were mixed overnight, washed on a glass filter, and dried for 5 hours in vacuum. The dry matter was 100%. 28% of the activity remained in the solution corresponding to a load of 22,300 LU/g.

EXAMPLE 26

Immobilization of purified lipase B 2.6 g dry weight of the carrier prepared in the previous example were used for the immobilization.

Lipase B (Example 10) was prepared as in Example 24, resulting in 24.9 ml of 3200 LU/ml.

Immobilization: Carrier and enzyme were mixed overnight, washed on a glass filter, and dried for 5 hours in vacuum. The dry matter was 100%. 6.4% of the activity remained in the solution corresponding to a load of 29,200 LU/g.

The activity was 4.4 BIU/g. A $NSI_2$ assay was run for 2 hours with 250 mg dry matter lipase and only 4 ml of reaction mixtures. The lauric acid incorporation was only 14 mole % and the $NSI_2$ was 0.65, indicating that lipase B is non-specific.

EXAMPLE 27

Properties of immobilized *C. antarctica* lipase and immobilized lipase A

The activity, thermostability, and non-specificity of immobilized *Candida antarctica* lipase from Example 22 and immobilized purified lipase A from Example 24 were compared.

The activity was measured both with the BIU assay (60° C., without organic solvent) and by the BTU assay at 70° C.

The non-specificity was measured both by the $NSI_1$ and $NSI_2$ assays.

The thermostability was measured by the following method:

1.2 g of triolein was added to 150 mg dry weight 10% hydrated enzyme. The sample was then incubated at 80° C. for 3 days. The remaining activity (BIU) was measured at 40° C. after addition of 12 ml of petroleum ether with 348 mg of palmitic acid. The thermostability is expressed in % of the activity of a reference sample placed for 3 days in a refrigerator.

The results are summarized in the table below:

| Enzyme: | Immob. C. antarctica | Immob. lipase A |
| --- | --- | --- |
| BIU/g (60° C., no solvent) | 41.9 | 21.4 |
| BTU/g (70° C.) | 186 | 128 |
| $NSI_2$ (at % obtained lauric acid incorporation) | 0.87 (58%) | 0.81 (58%) |
| $NSI_1$ | 0.67 | 0.75 |
| Thermostability, days at 80° C. | 78% | 69% |

The two immobilized products have very similar properties in all these tests. Both are non-specific, are effective for catalyzing acidolysis and transesterification, and both are extremely thermostable.

EXAMPLE 28

Activity and specificity of immobilized lipases

The following immobilized lipases were prepared as references:

A) 2.72 grams of *Candida cylindracea* lipase with activity 120,000 LU/g (product of Meito Sangyo Co.) was dissolved in 25 ml of water. 8.5 grams dry matter of Lewatit® E1999/85 weakly basic anion exchange resin (product of Bayer) was adjusted to pH 6 and mixed with the lipase solution. After rotation for 24 hours at room temperature and wash with water the preparation was dried in vacuum at room temperature giving 9.27 grams (dry matter content 97%). The activity remaining in the filtrate was 0.2% corresponding to a load of 28,000 LU/g dry matter immobilized lipase.

B) 2.0 grams of *Chromobacterium viscosum* lipase with activity 65,700 LU/g (product of Toyo Jozo, Japan) was dissolved in 25 ml of water. 4.25 grams dry matter of Duolite® ES-568N weakly basic anion exchange resin (product of Rohm & Haas, USA) was adjusted to pH 7 and mixed with the lipase solution. After rotation for 4 hours of room temperature the preparation was filtered, washed with water and dried in vacuum. The yield was 4.52 grams (dry matter 94%) and residual activity in the filtrate 6% corresponding to a load of 28,000 LU/g dry matter immobilized lipase.

The Non-Specificity Index (NSI$_2$) was measured as described previously in the specification, using immobilized *C. antarctica* lipase (preparation of Example 19), the two above preparations and immobilized *Mucor miehei* lipase (Lipozyme® IM 20, product of Novo Industri A/S).

In the table below fatty acid compositions are given in mole % following reactions for 2 hours at 60° C.

| Lipase preparation | Fatty acid composition | | | | |
|---|---|---|---|---|---|
| | La | P | S | Ol | NSI$_2$ |
| Invention: *Candida antarctica* | 62.8 | 9.6 | 14.4 | 13.2 | 0.96 |
| Reference: | | | | | |
| *Candida cylindracea* | 53.0 | 9.8 | 22.2 | 15.0 | 1.04 |
| *Chromobac. viscosum* | 31.4 | 10.0 | 25.4 | 33.1 | 0.02 |
| *Mucor miehei* | 45.5 | 8.5 | 13.1 | 33.0 | 0.02 |
| Cocoa butter stearin | 0.0 | 24.6 | 41.2 | 32.1 | — |

These results show that the two Candida ipases are positionally non-specific, and the Chromobacterium and Mucor lipases are 1,3-specific.

EXAMPLE 29

Thermostability of immobilized lipases

Thermostability of the immobilized preparations of *Candida antarctica* and *Candida cylindracea* lipases (Examples 19 and 28, respectively) was assayed as follows: 250 mg dry matter preparation was hydrated to 10% w/w. 600 mg triolein was added and incubations were made for 0, 2, 4, and 24 hours at 70° C. After incubation the sample was cooled, 12 ml petroleum ether containing 174 mg palmitic acid was added, and the mixture was incubated for 1 hour at 40° C. Incorporated palmitic acid (% w/w) in each case was measured, as described in the AF 206-method, referred to previously, as follows:

| Hours incubation | *C. antarctica* | *C. cylindracea* |
|---|---|---|
| 0 | 21.6 | 25.1 |
| 2 | 20.5 | 14.0 |
| 4 | 20.7 | 13.4 |
| 24 | 20.8 | 6.7 |

The results demonstrate the excellent thermostability of immobilized *C. antarctica* lipase, as it retains nearly all its activity after 24 hours at 70° C., whereas the prior-art lipase loses most of its activity.

By calculating as a first-order reversible reaction, it is estimated that *C. antarctica* lipase has retained approx. 90% activity after 24 hours at 70° C., and that the residual activity of *C. cylindracea* lipase is below 10%.

EXAMPLE 30

Acidolysis and transesterification with immobilized *C. antarctica* lipase

The immobilized product of Example 22 was used for acidolysis (triolein + palmitic acid) and transesterification (triolein + tripalmitin) without solvent at various temperatures according to the BIU and BTU methods.

Figure 5:
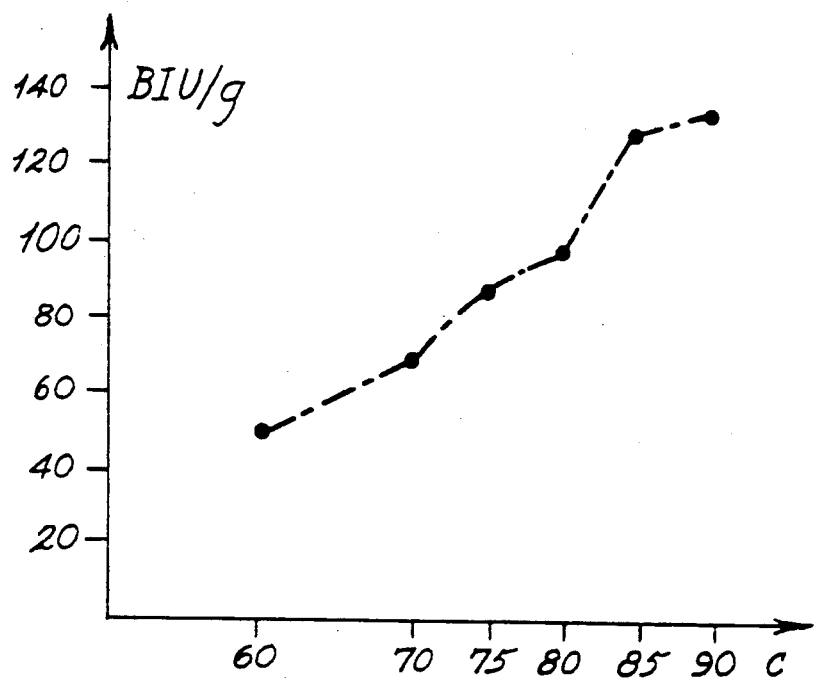
FIGS. 5 and 6 show the results of acidolysis and transesterification, respectively, with immobilized *C. antarctica* lipase at various temperatures. Details are given in Example 31.
Figure 6:
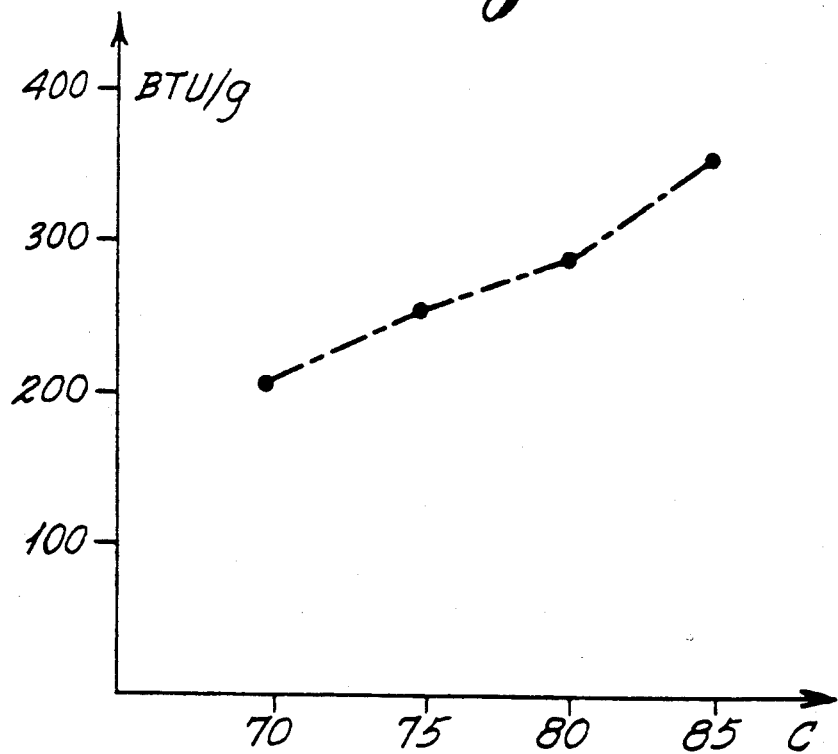

The activities (BIU and BTU) are shown in FIGS. 5 and 6, respectively. These clearly show the extreme thermostability of the immobilized lipase, as the highest activity was found at the highest temperatures tested, i.e. 85°-90° C.

EXAMPLE 31

Ester synthesis with immobilized *C. antarctica* lipases

The ability of immobilized *C. antarctica* (preparation from Example 22), immobilized purified lipase A (preparation from Example 25) and immobilized purified lipase B (preparation from Example 26) to catalyze ester synthesis were compared by the following method: 150 mg dry weight hydrated to 10% 20 hours before use, 1.5 milli-moles of alcohol (1-propanol, 2-propanol or oleyl alcohol (technical grade, BDH)) and 1.5 milli-moles of free fatty acid (myristic acid (grade 99%, Sigma) or oleic acid (92%, BDH)) were mixed in an 8 ml vial and shaken in a water bath at 60° C. Approx. 1 g samples were taken out after 20 minutes and 90 minutes incubation. 150 ml neutralized ethanol were added to the sample and the remaining free fatty acids were titrated by KOH. The obtained ester synthesis is calculated as 100% minus the titrated remaining free fatty acids.

The results are summarized in the table below:

| Immobilized enzyme | Alcohol | Free fatty acid | % obtained ester synthesis | |
|---|---|---|---|---|
| | | | after 20 min | after 90 min |
| Pure lipase A | 1-propanol | myristic acid | 10% | 22% |
| | 2-propanol | myristic acid | 7% | 16% |
| | oleyl alcohol | myristic acid | 14% | 52% |
| | 1-propanol | oleic acid | 12% | 15% |
| | 2-propanol | oleic acid | 14% | 15% |
| | oleyl alcohol | oleic acid | 12% | 36% |
| Pure lipase B | 1-propanol | myristic acid | 78% | 83% |
| | 2-propanol | myristic acid | 59% | 75% |
| | oleyl alcohol | myristic acid | 42% | 66% |
| | 1-propanol | oleic acid | 43% | 84% |
| | 2-propanol | oleic acid | 62% | 68% |
| | oleyl alcohol | oleic acid | 32% | 47% |
| *C. antarctica* lipase | 1-propanol | myristic acid | 82% | 84% |
| | 2-propanol | myristic acid | 43% | 71% |
| | oleyl alcohol | myristic acid | 34% | 82% |
| | 1-propanol | oleic acid | 62% | 90% |
| | 2-propanol | oleic acid | 38% | 65% |
| | oleyl alcohol | oleic acid | 43% | 83% |

It is seen that immobilized lipase B is more effective for ester synthesis than lipase A in all the experiments, both with long-chain and short-chain alcohol, and both with primary and secondary alcohol.

Immobilized lipase A gives low ester yields in case of short-chain alcohols, but is more effective in case of long-chain alcohol.

Immobilized *C. antarctica* lipase (containing both lipase A and lipase B) gives similar yield as lipase B for short-chain alcohol, and better yield than lipase A or B for long-chain alcohol.

EXAMPLE 32

Influence of fatty acid in acidolysis with immobilized lipase 250 mg dry matter of immobilized *C. antarctica* lipase (preparation from Example 22) or 150 mg dry matter of immobilized lipase A (preparation from Example 25) was hydrated to 10% in 20 hours and then mixed with 3 milli-moles of tricaprylin (Sigma grade II) and 3-milli-moles of one of the following fatty acids: Lauric acid (Merck art 805333), myristic acid (Sigma grade 99%), palmitic acid (BDH specially pure), stearic acid (Merck art 800673), oleic acid (Nu Check Prep 99%) and linoleic acid (Nu Check Prep 99%) in a 8 ml vial. The mixtures were incubated in shaking water bath at 70° C., samples were taken out after appropriate times to calculate the activity. The triglycerides were purified, methylated, analysed on GLC and the activities were calculated as described in the BIU method described previously. The results are summarized below:

|  | Activity<br>μ mole incorporated fatty acid<br>(initial activity) per minute |
|---|---|
| Immobilized *C. antarctiva* lipase: | |
| Acidolysis of tricaprylin with: | |
| lauric acid | 116 U/g |
| myristic acid | 100 U/g |
| palmitic acid | 121 U/g |
| stearic acid | 134 U/g |
| oleic acid | 74 U/g |
| linoleic acid | 56 U/g |
| Immobilized purified lipase A: | |
| Acidolysis of tricaprylin with: | |
| lauric acid | 13 U/g |
| oleic acid | 3 U/g |

EXAMPLE 33

Influence of fatty acid in acidolysis with immobilized lipase

In another experiment, 150 mg dry matter of immobilized *C. antarctica* lipase (preparation from Example 22) or immobilized purified lipase A (preparation from Example 25) was hydrated to 10% in 20 hours and then mixed with 3 milli-moles of each of the following reactants: trilaurin (Sigma grade 98%), palmitic acid (BDH, specially pure), oleic acid (Nu Check Prep, 99% pure), and linoleic acid (Nu Check Prep, 99% pure) in an 8 ml vial. The reaction mixtures were placed in shaking water bath at 70° C. Samples were taken out after 1½ and 3½ hours for immobilized *C. antarctica* lipase and after 1½ and 5½ for immobilized purified lipase A, the triglycerides were purified, methylated and analysed by GLC as described previously. The results are summarized below:

| Enzyme, immobilized | Purified lipase A | | *C. antarctica* lipase | |
|---|---|---|---|---|
| Reaction time | 1½ h | 5½ h | 1½ h | 3½ h |
| Triglyceride composition: | | | | |
| mole % lauric acid | 92.3 | 85.4 | 78.5 | 65.9 |
| mole % palmetic acid | 5.0 | 10.1 | 9.3 | 14.5 |
| mole % oleic acid | 1.7 | 2.6 | 6.4 | 10.1 |
| mole % linoleic acid | 0.7 | 1.7 | 5.8 | 9.4 |

It is seen that lipase A has a much lower activity towards mono- and di-unsaturated acid than towards saturated acid. *C. antarctica* lipase (containing both lipase A and lipase B) has only slightly lower activity towards mono- and di-unsaturated acid.

EXAMPLE 34

Acidolysis of immobilized lipases with poly-unsaturated fatty acid

The ability of immobilized *C. antarctica* (the preparation from Example 22), immobilized purified lipase A (the preparation from Example 25) and immobilized specific lipase from *Mucor miehei* (Lipozyme ® IM 20 from NOVO INDUSTRI A/S) to incorporate poly-unsaturated fatty acids into triglycerides were compared by mixing 250 mg dry matter of immobilized lipase (hydrated to 10% water), 1276 mg trilaurine (Sigma grade 98%) and 2500 mg fatty acid mixture in an 8 ml vial. The fatty acid mixture was obtained by mixing palmitic acid with a poly-unsaturated fatty acid rich fraction (obtained by vacuum distillation) from hydrolyzed Menhaden oil. The fatty acid mixture contained 24.9 mole % palmitic acid (C16:0), 20.4 mole % eicosapentaenoic acid (C20:5), 7.2 mole % docosapentaenoic acid (C22:5) and 26.2 mole % docosahexanoic acid (C22:6). The reaction was carried out in a shaking water bath at 70° C. Samples were taken out after 3 and 5 hours, and the triglycerides were purified, methylated, and analysed by GLC as described previously.

The fatty acid composition of the triglycerides (in mole %) and ratios between these are shown below:

|  | INVENTION | | | | REFERENCE | |
|---|---|---|---|---|---|---|
|  | Immobilized lipase | | | | | |
|  | Pure lipase A | | *C. antarctica* | | *Mucor miehei* | |
|  | Reaction time in hours | | | | | |
|  | 3 | 5 | 3 | 5 | 3 | 5 |
| Fatty acid: | | | | | | |
| lauric (C12:0) | 63.8 | 54.1 | 40.4 | 41.5 | 62.7 | 53.9 |
| palmitic (C16:0) | 16.4 | 20.8 | 17.4 | 16.4 | 15.2 | 15.9 |
| C20:5 | 4.1 | 7.1 | 11.6 | 12.5 | 6.2 | 8.5 |
| C22:5 | 1.2 | 3.0 | 4.1 | 4.7 | 2.4 | 4.8 |
| C22:6 | 2.8 | 5.4 | 13.0 | 14.3 | 2.4 | 3.2 |
| Ratios: | | | | | | |
| $\frac{C20:5}{C16:0}$ | 0.25 | 0.34 | 0.67 | 0.76 | 0.41 | 0.53 |
| $\frac{C22:6}{C16:0}$ | 0.17 | 0.46 | 0.75 | 0.87 | 0.16 | 0.20 |

It is seen that *C. antarctica* lipase is effective in incorporating poly-unsaturated fatty acid, almost with the same ease as for saturated acid. The two lipases of the invention are effective in incorporating C22:6 acid.

EXAMPLE 35

Ester synthesis with immobilized lipase

Illustration of the difference in activity of lipase from *Candida antarctica* and a 1,3-positionally specific lipase from *Mucor miehei* in synthesis of esters from primary and secondary alcohols.

11.42 g (0.05 moles) of myristic acid (Merck, purity 98%) and 3.01 g (0.05 moles) of n-propanol or isopropanol (Merck, purity 99%) was shaked together at 60° C. with 1 g of an immobilized lipase. Either an immobilized lipase from *Candida antarctica* (preparation from Example 22) adjusted to 10% water content or a commercially available 1,3-positionally specific lipase from *Mucor miehei* (Lipozyme ® IM 20).

The esterification reaction was followed by taking out samples and titrating the non-reacted fatty acid (as described in Example 31).

Figure 7:
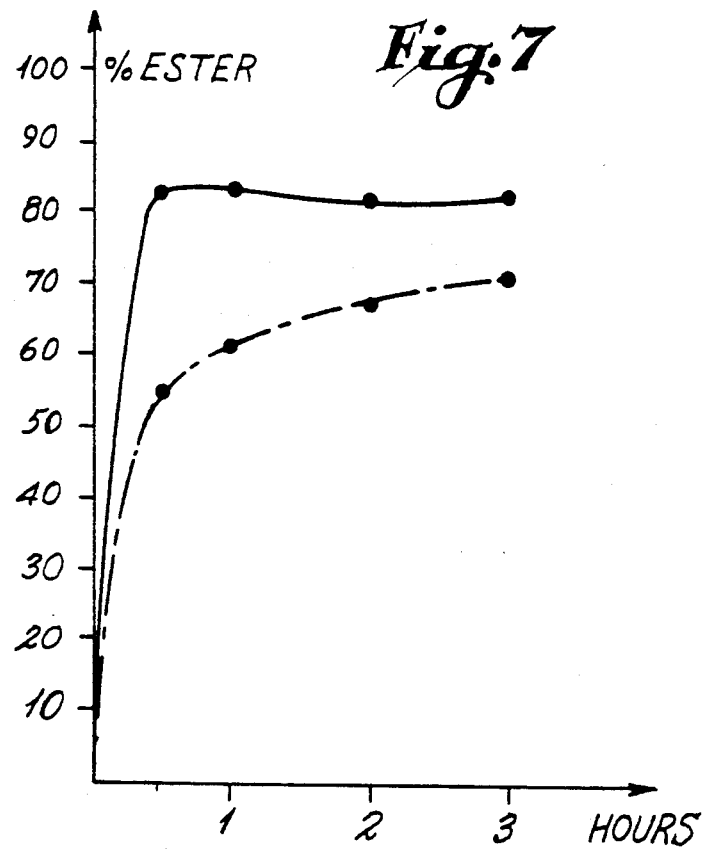
FIGS. 7 and 8 show the results of myristic acid ester synthesis with immobilized *C. antarctica* lipase, using n-propanol and isopropanol, respectively. Details are given in Example 37.
Figure 8:
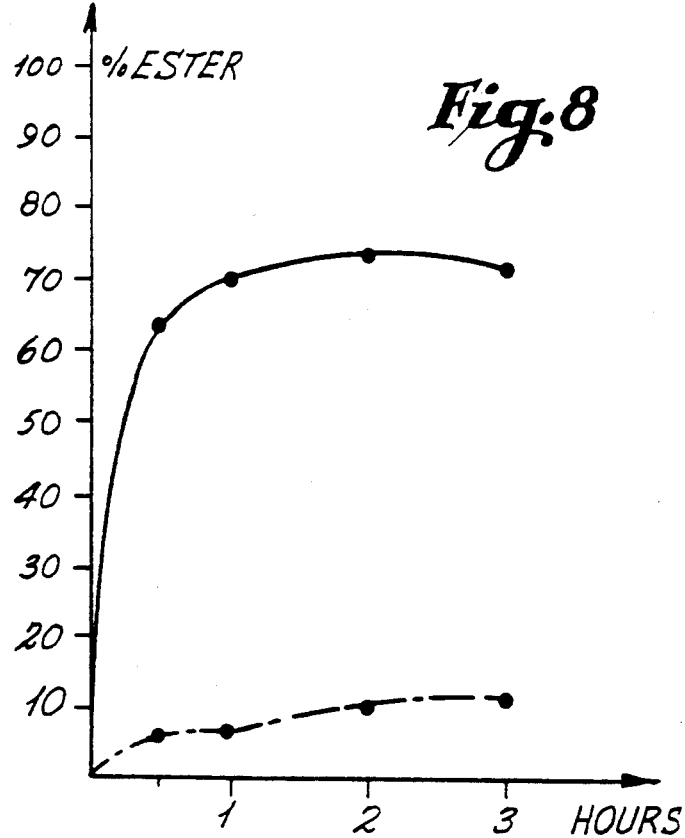

Results with n-propanol and isopropanol are shown in FIG. 7 and 8, respectively.

The results show that *C. antarctica* lipase is effective for ester synthesis with both primary and secondary alcohol, whereas the positionally specific Mucor lipase is only effective on primary alcohol.

The ability of *Candida antarctica* lipase to synthesize long-chain esters was also examined.

11.42 g (0.05 moles) of myristic acid (Merck, purity 98%) and 10.72 g (0.05 moles) of myristic alcohol (Merck, purity 98%) was reacted together with the immobilized lipase (preparation from Example 22) under vacuum at 60° C. Measured % ester is shown below:

| Reaction time | Enzyme dosage | |
| --- | --- | --- |
| | 1 g | 0.2 g |
| ½ hour | 98% | 57% |
| 1 | 98% | 86% |
| 2 | — | 97% |
| 3 | — | 98% |

The results demonstrate that *C. antarctica* lipase is effective for ester synthesis both with short-chain and long-chain alcohols.

EXAMPLE 36

Continuous acidolysis 4.5 g of the immobilized *C. antarctica* lipase (Example 21) was filled into a water jacketed column, having an internal diameter of 1.5 cm.

The column was equipped with a water jacket with hot circulating water and was kept at 60° C. or 80° C. A precolumn containing water-saturated resin, (Duolite ® ES561) was placed before the enzyme column and kept at the same temperature. A substrate consisting of 71% highly refined soy bean oil with a peroxide value less than 3 and 29% analytical grade lauric acid was pumped through the columns. At the outlet from the enzyme column samples were taken for analysis, and the incorporation of lauric acid measured by GLC. An incorporation of 14% w/w lauric acid was attempted and the flow rate was adjusted in order to keep the conversion at that value. Measurements of flow rate were taken when the actual conversion was 14±1%. Whenever the precolumn was dry it was replaced by a fresh one.

The samples were analysed by removing the free fatty acid and mono- and diglyceride by $Al_2O_3$-column chromatography, thereafter methylation of the triglyceride by $NaOCH_3$ and finally analysis of the methylester on a GLC.

Figure 9:
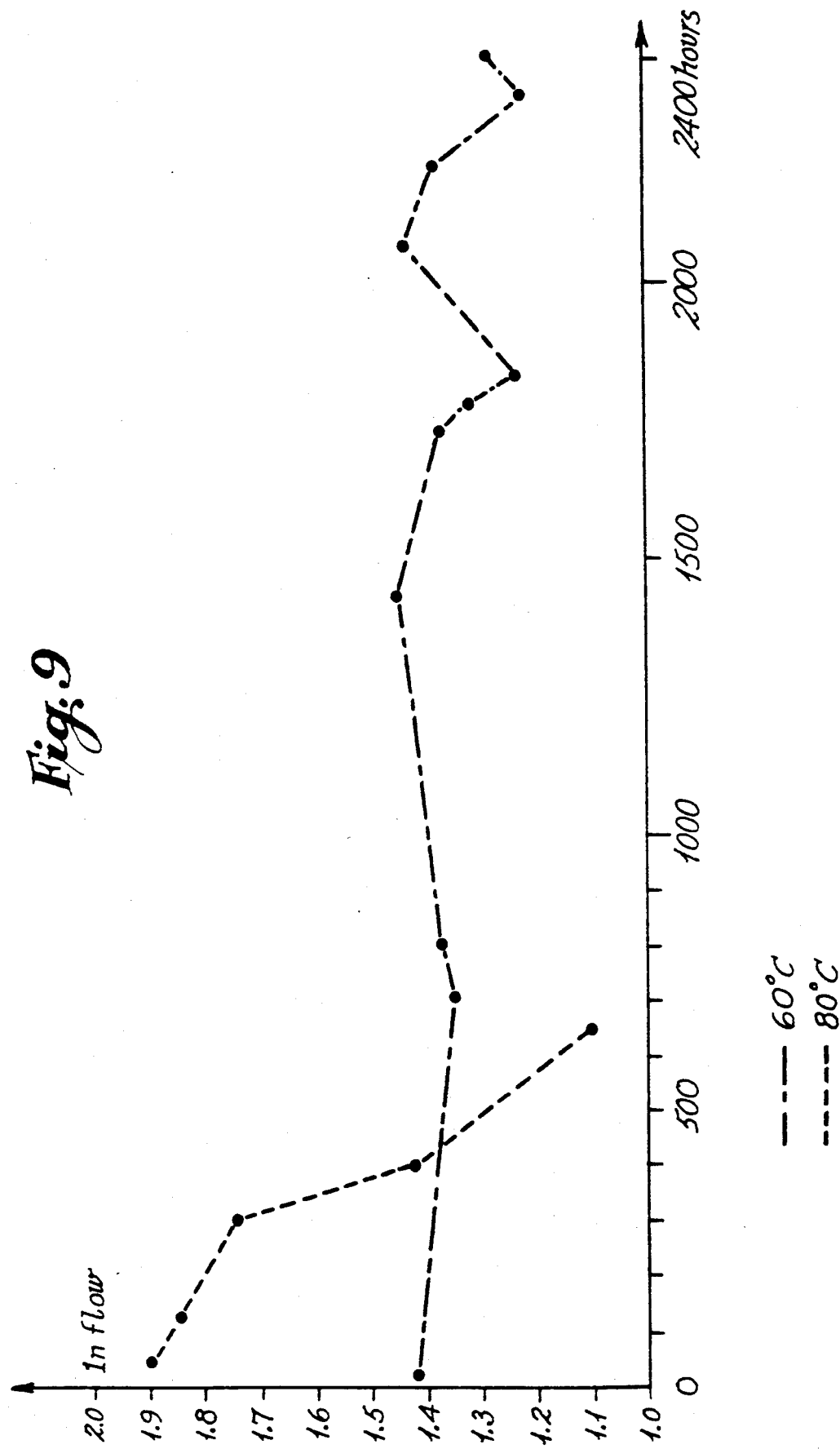
FIG. 9 and 10 show the results of continuous acidolysis and transesterification, respectively with immobilized *C. antarctica* lipase. Details are given in Examples 36 and 39.

The results are shown in FIG. 9 as the natural logarithm of flow rate (g triglyceride/hour/g immobilized enzyme) versus time (hours). It is seen that at 60° C. the lipase activity is nearly constant in 2,400 hours, i.e. the preparation is extremely stable.

EXAMPLE 37

Fat hydrolysis

Olive oil was hydrolyzed at 60° C. with *C. antarctica* lipase (prepared as in Example 2) in an 8 l thermostated tank with stirring. The oil:water ratio was 60:40 or 70:30 (w/w), and the lipase dosage was 75 LU/g of oil. Results (% hydrolysis) were as follows:

| Time, hours | Oil:water ratio | |
| --- | --- | --- |
| | 60:40 | 70:30 |
| 24 | 80 | 70 |
| 48 | 91 | 85 |
| 72 | 93 | 89 |
| 96 | 95 | 91 |

It is seen that essentially complete hydrolysis can be obtained, and that the lipase continues to be active even after 4 days at 60° C.

EXAMPLE 38

Thermostability of lipases after heat treatment

Lipases from *C. antarctica* (0.1% solution of powder from Example 1), *C. tsukubaensis* (3% from Example 5) and *C. auriculariae* (3% from Example 6) were tested.

Each enzyme solution was first pretreated at 60° C. for 1 hour and then incubated for 30 minutes at 0°, 40°, 50°, 60°, 70° or 80° C. Activities were measured by the OU method.

| | C. antarctica | C. tsukubaensis | C. auriculariae |
| --- | --- | --- | --- |
| Remaining activity after pre-treatment 30 minutes at | 34.7% | 60.6% | 65.2% |
| 0° C. | 100% | 100% | 100% |
| 40° C. | 107% | 104.2% | 93.3% |
| 50° C. | 93.3% | 116.1% | 88.8% |
| 60° C. | 98.7% | 115.4% | 88.8% |
| 70° C. | 89.7% | 60.8% | 15.2% |
| 80° C. | 94.2% | 0 | 0 |

It is seen that heat-treated *C. antarctica* lipase is extremely thermostable, even at 80° C. Heat-treated *C. tsukubaensis* lipase is stable up to 70° C., and heat-treated *C. auriculariae* lipase up to 60°-70° C.

EXAMPLE 39

Continuous transesterification

Immobilized lipase of Example 23 was used at 60° C. with a substrate mixture of equal volumes of palm oil mid fraction and soy bean oil. Other conditions were as in Example 36.

Outlet samples were analyzed by HPLC, and flow rate was adjusted to an attempt to keep the content of trilinolein in the outlet near 6%. This represents about 63% of equilibrium conversion, as the inlet content was 11.0%. Measurements were taken when the outlet content was 6%±1%.

Figure 10:
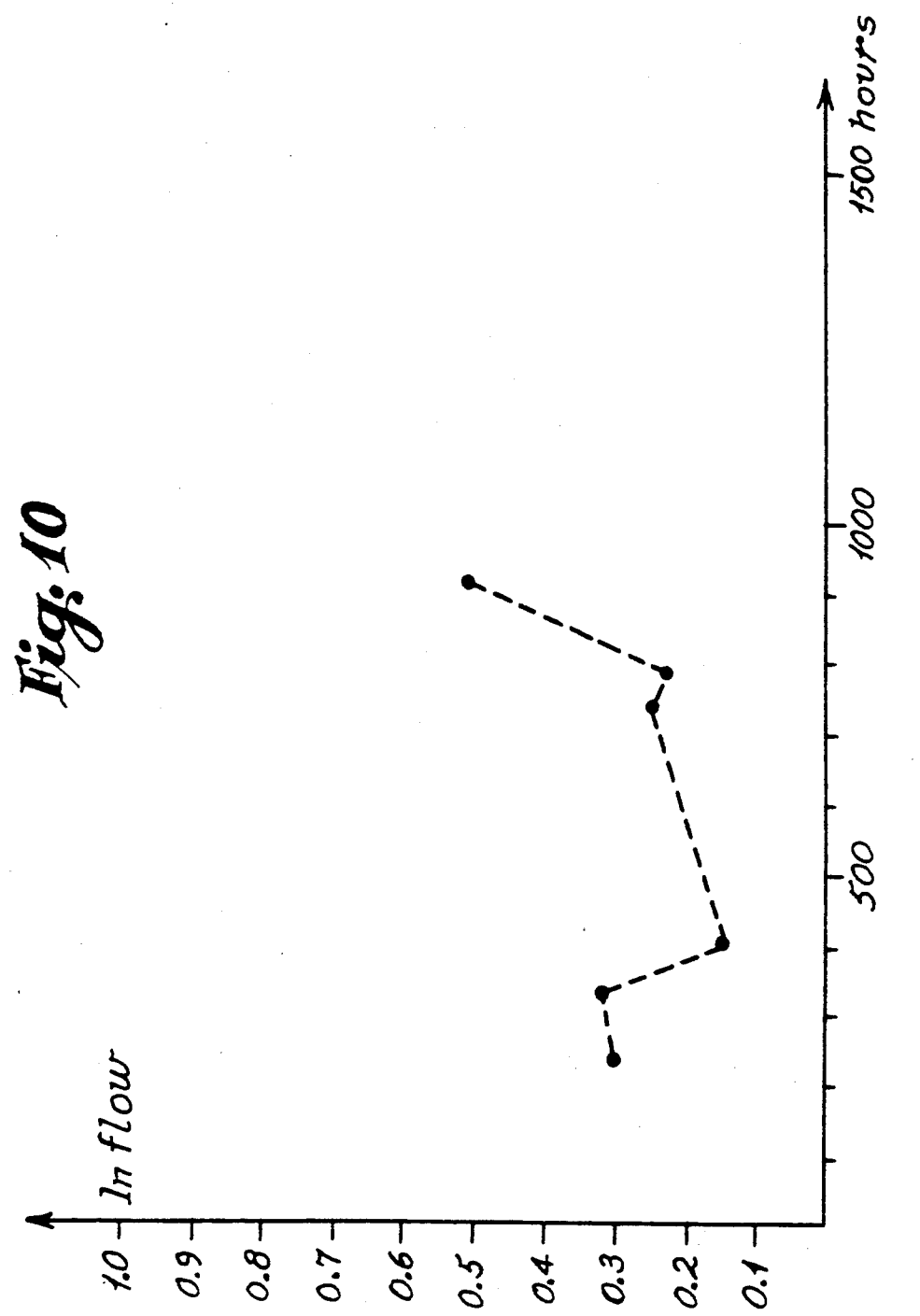

The results are shown in FIG. 10 in the same way as FIG. 9 (Example 36). The flow rate shows approx. ±20% variation, but no deactivation is seen in approx. 1,000 hours of operation at 60° C.

I claim:

1. An isolated lipase which (1) is positionally non-specific, (2) retains at least 50% of its activity after incubation for 30 minutes at 60° C., (3) has optimum activity around pH 7 to 8, and (4) shows immunochemical identity with an extracellular lipase produced by a Candida strain selected from the group consisting of *C. antarctica, C. tsukubaensis, C. auriculariae, C. humicola* and *C. foliorum*.

2. The lipase according to claim 1, wherein the Candida strain is selected from the group consisting of *C. antarctica* DSM 3855, DSM 3908, DSM 3909, CBS 5955, CBS 6678, CBS 6821, *C. tsukubaensis* CBS 6389, *C. auriculariae* CBS 6379, *C. humicola* CBS 571, CBS 2041, IFO 1527 and *C. foliorum* CBS 5234.

3. An isolated lipase which (1) is positionally non-specific, (2) retains at least 20% of its activity after incubation for 60 minutes at pH 6.5, 65° C. (3) has optimum activity around pH 7 to 8, and (4) shows immunochemical identity with an extracellular lipase produced by a Candida strain selected from the group consisting of *C. antarctica* and *C. tsukubaensis*.

4. The lipase according to claim 3, wherein the Candida strain is selected from the group consisting of *C. antarctica* DSM 3855, DSM 3908, DSM 3909, CBS 5955, CBS 6678, CBS 6821 and *C. tsukubaensis* CBS 6389.

5. The lipase according to claim 4, wherein said lipase has a temperature optimum of about 65° C. and wherein the strain is *C. antarctica* DSM 3855.

6. The lipase according to claim 5 which has a molecular weight of about 43 kD and an isoelectric point of about 8.0.

7. The lipase according to claim 5 which has a molecular weight of about 33 kD and an isoelectric point of about 6.0.

8. The lipase according to claim 66 or 3 in immobilized form.

9. The lipase according to claim 8, wherein said immobilized lipase has a half-life of lipase activity at 60° C. in excess of 1000 hours in continuous interesterification.

10. The lipase according to claim 9, wherein the lipase is immobilized by adsorption on a weakly basic anion exchange resin or on an adsorbent resin.

11. A method for producing the lipase according to claim 1, said method comprising (1) aerobically cultivating a lipase producing Candida strain selected from the group consisting of *C. antarctica, C. tsukubaensis, C. auriculariae, C. humicola* and *C. foliorum*, and (2) recovering the lipase.

12. A method for producing the lipase according to claim 3, said method comprising (1) aerobically cultivating a lipase producing Candida strain selected from the group consisting of *C. antarctica* and *C. tsukubaensis*, and (2) recovering the lipase.

13. The method according to claim 12, further comprising heating the recovered lipase for 1–3 hours at about 60° C.

14. The method according to claim 12, further comprising immobilizing the recovered lipase.

15. A process for hydrolyzing, synthesizing or interesterifying an ester comprising (a) reacting the ester with water, reacting an acid with an alcohol or interesterifying the ester with an acid, an alcohol or a second ester, wherein the reaction is catalyzed by the lipase according to claim 3 and (b) recovering the products of the hydrolysis, synthesis or interesterification.

16. The process according to claim 15, wherein the lipase is in immobilized form.

17. The process according to claim 16, wherein the process is continuous.

18. The process according to claim 15, wherein the ester is a triglyceride.

19. The process according to claim 15, wherein the strain is a *C. antarctica* strain.

20. The process according to claim 19, wherein the process is interesterification and the lipase is has a molecular weight of about 43 kD and an isoelectric point of about 8.0.

21. The process according to claim 19, wherein the process is ester synthesis and the lipase has a molecular weight of about 33 kD and an isoelectric point of about 6.0.

* * * * *